(12) United States Patent
Harrison et al.

(10) Patent No.: US 7,695,441 B2
(45) Date of Patent: Apr. 13, 2010

(54) AUTOMATED DIAGNOSTIC HEARING TEST

(75) Inventors: Jeffrey S. Harrison, Palo Alto, CA (US); Aaron Thornton, West Des Moines, IA (US); Christopher L. Wasden, Sugar Land, TX (US); Barry Strasnick, Virginia Beach, VA (US); Kenneth R. Stott, Sugar Land, TX (US)

(73) Assignee: Tympany, LLC, The Woodlands, TX (US)

( * ) Notice: Subject to any disclaimer, the term of this patent is extended or adjusted under 35 U.S.C. 154(b) by 79 days.

(21) Appl. No.: 10/439,958

(22) Filed: May 15, 2003

(65) Prior Publication Data

US 2004/0006283 A1    Jan. 8, 2004

Related U.S. Application Data

(60) Provisional application No. 60/383,303, filed on May 23, 2002, provisional application No. 60/466,313, filed on Apr. 29, 2003.

(51) Int. Cl.
*A61B 5/00* (2006.01)
(52) U.S. Cl. .................................................. 600/559
(58) Field of Classification Search ............... 600/559, 600/300; 73/585
See application file for complete search history.

(56) References Cited

U.S. PATENT DOCUMENTS

| 3,054,855 | A |   | 9/1962 | Hyman |
| 3,134,861 | A |   | 5/1964 | Dempsey |
| 3,623,241 | A |   | 11/1971 | Horner et al. |
| 3,809,811 | A | * | 5/1974 | Delisle et al. ............... 73/585 |

(Continued)

FOREIGN PATENT DOCUMENTS

GB    2351838 A    1/2001

(Continued)

OTHER PUBLICATIONS

Gerald A. Studebaker, et al., *Frequency-Importance and Transfer Functions for Recorded CID W-22 Word Lists*, Journal of Speech and Hearing Research; Apr. 1991, pp. 427-438; vol. 34.

(Continued)

*Primary Examiner*—Max Hindenburg
*Assistant Examiner*—Jonathan M Foreman
(74) *Attorney, Agent, or Firm*—Locke Lord Bissell & Liddell LLP

(57) ABSTRACT

Method and system are disclosed for automated testing of a patient's hearing. The automated hearing test allows the patient to quickly and accurately test his own hearing with minimal or no assistance from an audiologist or other hearing health professionals. The test prompts and instructs the patient for inputs and responses as needed. The patient can select one or several tests to be performed, including air and bone conduction testing with masking, speech reception threshold, speech discrimination, tympanogram, acoustic reflex, and otoacoustic emissions testing. Multiple languages are supported. Data obtained from one test may be used for another test or another iteration of the same test to calculate masking levels. The automatic hearing test also detects ambient noise and can compensate for it in the test results. If a contingency occurs, the automated hearing test is configured to page the operator for assistance.

23 Claims, 13 Drawing Sheets

U.S. PATENT DOCUMENTS

| | | | |
|---|---|---|---|
| 5,197,332 A * | 3/1993 | Shennib | 73/585 |
| 5,323,468 A | 6/1994 | Bottesch | |
| 5,645,074 A | 7/1997 | Shennib et al. | |
| 5,811,681 A | 9/1998 | Braun et al. | |
| 6,160,893 A | 12/2000 | Saunders et al. | |
| 6,168,563 B1 | 1/2001 | Brown | |
| 6,201,875 B1 | 3/2001 | Davis et al. | |
| 6,331,164 B1 | 12/2001 | Shaw et al. | |
| 6,366,863 B1 | 4/2002 | Bye et al. | |
| 6,377,925 B1 | 4/2002 | Greene et al. | |
| 6,379,314 B1 | 4/2002 | Horn | |
| 6,396,930 B1 | 5/2002 | Vaudrey et al. | |
| 6,416,482 B1 | 7/2002 | Braun et al. | |
| 6,428,485 B1 | 8/2002 | Rho | |
| 6,447,461 B1 | 9/2002 | Eldon | |
| 6,496,585 B1 * | 12/2002 | Margolis | 381/60 |
| 6,644,120 B1 | 11/2003 | Braun et al. | |
| 6,647,345 B2 | 11/2003 | Bye et al. | |
| 6,674,862 B1 | 1/2004 | Magilen | |
| 6,730,041 B2 | 5/2004 | Dietrich | |
| 2001/0049480 A1 | 12/2001 | John et al. | |
| 2002/0016554 A1 | 2/2002 | Iseberg | |
| 2002/0026125 A1 | 2/2002 | Leysieffer | |
| 2002/0068986 A1 | 6/2002 | Mouline | |
| 2002/0076056 A1 | 6/2002 | Pavlakos | |
| 2002/0107692 A1 | 8/2002 | Litovsky | |
| 2002/0136365 A1 | 9/2002 | D'Agri | |
| 2002/0165466 A1 | 11/2002 | Givens et al. | |
| 2003/0083591 A1 | 5/2003 | Edwards et al. | |
| 2004/0006283 A1 | 1/2004 | Harrison et al. | |
| 2004/0039299 A1 | 2/2004 | Harrison et al. | |
| 2004/0049125 A1 * | 3/2004 | Nakamura | 600/559 |
| 2004/0064066 A1 * | 4/2004 | John et al. | 600/559 |
| 2004/0068200 A1 | 4/2004 | Harrison et al. | |
| 2004/0071295 A1 | 4/2004 | Wasden et al. | |
| 2004/0071296 A1 | 4/2004 | Wasden et al. | |
| 2004/0073134 A1 | 4/2004 | Wasden et al. | |
| 2004/0073135 A1 | 4/2004 | Wasden et al. | |
| 2004/0073136 A1 | 4/2004 | Thorton et al. | |
| 2004/0097826 A1 | 5/2004 | Harrison et al. | |
| 2004/0097839 A1 | 5/2004 | Epley | |
| 2004/0152998 A1 | 8/2004 | Stott et al. | |
| 2005/0033193 A1 | 2/2005 | Wasden et al. | |

FOREIGN PATENT DOCUMENTS

| | | |
|---|---|---|
| JP | 05030599 A | 2/1993 |
| NL | 8400196 | 8/1984 |
| WO | 8707464 A | 12/1987 |
| WO | WO9841973 | 9/1998 |
| WO | 0065983 A | 11/2000 |
| WO | WO0106916 | 2/2001 |
| WO | WO02062221 | 8/2002 |
| WO | 2004104761 | 12/2004 |

OTHER PUBLICATIONS

Aaron R. Thornton, et al., *Speech-Discrimination Scores Modeled as a Binomial Variable*, Journal of Speech and Hearing Research, Sep. 1978, pp. 507-518; vol. 21, No. 3.

Chris Haplin, Ph.D., et al., *The articulation index in clinical diagnosis and hearing aid fitting*, Current Opinion in Otolaryngology & Head and Neck Surgery, 1996, pp. 325-334; Rapid Science Publishers.

*The Audiology Primer for Students and Health Care Professionals*; Summer, 1997, pp. i-69; Department of Veterans Affairs.

International Search Report for PCT/US03/16200 dated Jul. 28, 2004.

International Search Report for PCT/US04/15329 dated Nov. 16, 2004.

International Search Report for PCT/US04/15328 dated Nov. 19, 2004.

Gelfand, S.A., *Essentials of Audiology*, 2d ed., Thieme Medical Publishers, Inc., 2001.

McCullough et al., *A multimedia approach for estimating speech recognition of multilingual clients*, AJA, Mar. 1994, pp. 19-22.

Matsuhira, Toshimasa, *Improved method of masking in pure tone audiometry—use of minimum level masking*, Practica Oto-Rhino-Laryngologica, 82:11; 1541-1540, 1989.

Smith, Brenda L. and Markides, Andreas, *Interaural attenuation for pure tones and speech*, British Journal of Audiology, 15:40 9-54, 1981.

Thornton, Aaron, *Computer-Assisted Audiometry and Technicians in a High-Volume Practice*, Nov. 1993 AJA, pp. 11-13.

Barry, S. Joseph, *Can Bone Conduction Thresholds Really Be Poorer Than Air?*, Nov. 1994 AJA, pp. 21-22.

M.S. Dean and F.N. Martin, *Insert Earphone Depth and the Occlusion Effect*, AJA, vol. 9, 159-0889, Sep. 5, 2000.

J.A. McCullough, R.H. Wilson, J.D. Birck and L.G. Anderson, *A Multimedia Approach for Estimating Speech Recognition of Multilingual Clients*, Mar. 1994 AJA, pp. 19-22.

R.H. Wilson and J.K. Antablin, *A Picture Identification Task as an Estimate of the Word-Recognition Performance of Nonverbal Adults*, Journal of Speech and Hearing Disorders, May 1980, vol. 45, No. 2.

European Search Report for Corresponding European Patent Application EP03755440.9.

International Search Report for Corresponding International Application No. PCT/US06/34324.

Written Opinion for for Corresponding International Application No. PCT/US06/34324.

International Search Report for Corresponding International Application No. PCT/US06/34357.

Written Opinion for for Corresponding International Application No. PCT/US06/34357.

Rogers, J., "Audiology Policy for Stenger Screening Test." Conwy & Denbighshire NHS Trust. Apr. 2002 [retrieved on Apr. 3, 2007]. Retrieved from the Internet: <URL:http://www.glanclwyd.demon.co.uk/audiology/clinprot/stengerscreeningpolicy.htm>, entire document.

European Supplementary Search Report for Corresponding European Patent Application EP04752359.2.

European Supplementary Search Report for European Patent Application No. 04752358.4, dated Apr. 24, 2009.

* cited by examiner

AUTOMATED DIAGNOSTIC HEARING TEST

CROSS-REFERENCE TO RELATED APPLICATION

This application for patent claims the benefit of priority from, and hereby incorporates by reference, U.S. Provisional Patent Application Ser. No. 60/383,303, entitled "Audiometer," filed on May 23, 2002, and U.S. Provisional Patent Application Ser. No. 60/466,313, entitled "System and Method for Conducting Multiple Diagnostic Hearing Tests," filed on Apr. 29, 2003.

BACKGROUND OF THE INVENTION

1. Field of the Invention

This invention is directed in general to the field of audiology and in particular to an automated method and system for assessment and analysis of hearing loss.

2. Description of the Related Art

According to recent studies, over 20 million people in the United States alone have some degree of hearing loss. The number of people worldwide who have some degree of hearing loss is estimated to be much greater. Not surprisingly, many of these people are unaware that they have suffered a decrease in hearing capacity. The decreased hearing capacity may be due to several factors including age, health, occupation, injury, and disease. This loss of hearing can lead to significant reductions in quality of life, impaired relationships, reduced access to employment and diminished productivity. Failure to treat the hearing loss may worsen the impact. According to the Better Hearing Institute, the annual cost in the United States in terms of lost productivity, special education, and medical care because of untreated hearing loss is approximately $56 billion. Much of this staggering cost can be reduced or prevented by early detection and treatment. Unfortunately, few people obtain regular and frequent hearing tests as a part of their routine healthcare due, in part, to the lack of a simple, convenient, and relatively inexpensive hearing test.

Traditionally, a hearing test is conducted in a clinical setting by a hearing health professional, such as an audiologist, who administers the hearing test manually. The hearing health professional controls an audiometer to produce a series of tones that each have a very specific frequency and intensity. The term "intensity" as used herein refers to the amplitude of the tone and is usually stated in decibels (dB). The tones are then conducted through a transducer, such as earphones or ear inserts, to the patient in a quiet room or sound isolation booth. For each audible tone, the patient gestures or otherwise indicates that he has heard the tone. If the tone is not audible, the patient does not respond. The hearing health professional thereafter adjusts the intensity level of the tone in preset increments until it becomes audible to the patient. By repeating this process for several different tones and compiling the results, the hearing health professional is able to determine the extent of the hearing loss, if any.

An advantage of having a hearing health professional manually administer the hearing test is the hearing health professional can apply his considerable training and experience during the test. For example, by simply talking to the patient and varying the loudness of his voice, the hearing health professional can determine an initial intensity level at which to start the tones and sounds. Furthermore, the hearing health professional can adapt the pace of the test as needed to accommodate a tired or uncooperative patient. More importantly, the hearing health professional can discern between false responses or guesses and responses that are legitimate. Finally, the hearing health professional can adjust the results of the hearing test as needed to reflect extenuating circumstances or problems, such as excessive ambient noise, equipment limitations, and other similar factors.

Like most highly trained and specialized medical professionals, however, a hearing health professional's time and services are usually very expensive. Accessibility and convenience can also be issues, as there are fewer hearing health professionals relative to other types of medical professionals. And while hearing health professionals are highly trained, they are limited in their ability to make rapid and accurate calculations of the test data and have to rely on approximations and rules of thumb for guidance in many instances. In addition, few hearing health professionals in the United States can speak a foreign language. As a result, traditional hearing tests are almost always administered in English, which can be a problem for non-English speaking patients.

Other drawbacks of the traditional, manually administered hearing tests include the need for a quiet room or sound isolation booth in order to properly conduct the tests. The quiet room or sound isolation booth has to comply with ANSI (American National Standards Institute) requirements in terms of how much noise may penetrate the room or booth during a test. Typically, a specially trained technician must evaluate and certify the quiet room or sound isolation booth as meeting ANSI standards before the room or booth can be used. At present, there are relatively few technicians who are trained to perform such evaluations and certifications. All the above factors combine to increase the complexity of the traditional hearing tests and thereby discourage or at least contribute to a general lack of interest by most people in obtaining regular and frequent hearing tests.

One attempt to simplify the traditional hearing test involves the use of a computer network, such as the Internet, to administer the test. The computer network facilitates interaction between a centralized test administration site and remotely located patient sites. Such an arrangement makes it possible (or at least more convenient) for people in remote or rural areas to obtain a hearing test. And the hearing test can be performed so that it meets standardized guidelines such as ANSI requirements or certification standards. Despite the increased convenience, a hearing health professional must still manually administer the test, albeit remotely. In this regard, the test is very similar to the traditional hearing test and has many of the same shortcomings.

Accordingly, what is needed is a hearing test that overcomes the shortcomings of the traditional hearing test. Specifically, what is needed is a hearing test that is simpler, more convenient, less expensive, can be administered by the patient rather than by the hearing health professional, yet does not compromise the accuracy or thoroughness of the traditional, manually administered hearing test.

SUMMARY OF THE INVENTION

The present invention is directed to a method and system for automated testing of a patient's hearing. The automated hearing test allows the patient to quickly and accurately test his own hearing with minimal or no assistance from an audiologist or other hearing health professionals. The test prompts and instructs the patient for inputs and responses as needed. The patient can select one or several tests to be performed, including air and bone conduction testing with masking, speech reception threshold, speech discrimination, and tympanogram/acoustic reflex testing. Multiple languages are supported. Data obtained from one test may be used for another test or another iteration of the same test to calculate masking levels. The automatic hearing test also detects ambient noise and can compensate for it in the test results. If a contingency occurs, the automated hearing test is configured to page the operator for assistance.

BRIEF DESCRIPTION OF THE DRAWINGS

A better understanding of the invention may be had by reference to the following detailed description when taken in conjunction with the accompanying drawings, wherein.

DETAILED DESCRIPTION OF THE INVENTION

Figure 1:
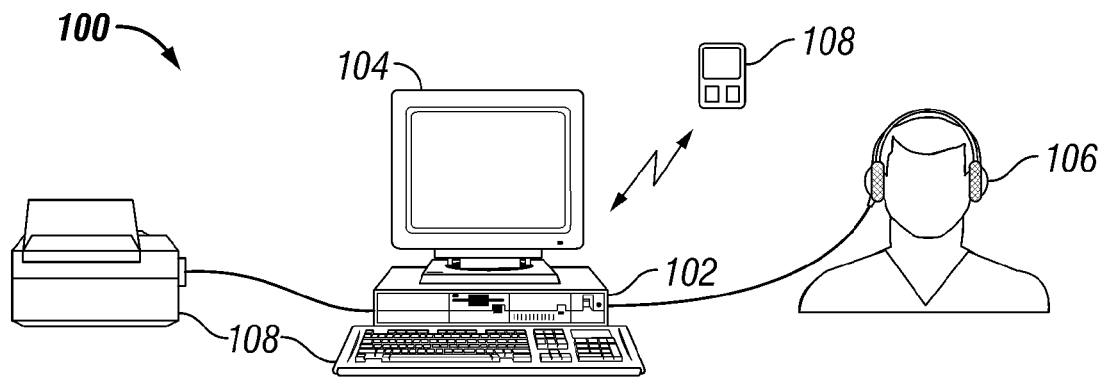
FIG. 1 illustrates an exemplary system for providing an automated hearing test according to embodiments of the invention.

Following is a detailed description of the invention with reference to the drawings wherein reference numerals for the same or similar elements are carried forward.

As mentioned above, the present invention is directed to a method and system for automated testing of a patient's hearing. The term "automated testing" as used herein refers to testing that is performed primarily by a computer, as opposed to testing that is performed primarily by a hearing health professional. The automated hearing test allows the patient to test his own hearing with minimal or no assistance from an audiologist or other hearing health professional. Typically, an operator, such as the hearing health professional or a trained assistant, helps the patient with the initial set up (e.g., seating, putting on the headset, demonstrating button usage, etc.) and explains how the test works. Thereafter, the automated hearing test prompts and instructs the patient for all inputs and responses needed. If a contingency occurs, for example, the patient falls asleep, the automated hearing test alerts (e.g., by paging) the operator as needed. Such a patient-administered hearing test can be simpler, more convenient, and less expensive than the traditional, audiologist-administered test.

In addition, the hearing test of the present invention provides an accurate and thorough assessment of the patient's hearing. The automated hearing test includes air and bone conduction testing with masking, speech reception threshold testing, speech discrimination testing, and can accommodate tympanogram, acoustic reflex, otoacoustic emission, and acoustic immitance testing. The tests are performed in a manner to comply with relevant standards and guidelines such as ANSI requirements and other standards. Furthermore, the automated hearing test can detect and compensate for ambient noise and, therefore, does not require the use of a certified quiet room or sound isolation booth. Finally, the automated hearing test can be configured for any number of languages for patients in all parts of the world.

Hearing health professionals will also benefit from the automated hearing test of the present invention. Although the test itself requires little or no intervention, a hearing health professional still must analyze the test results and recommend treatment. Therefore, the automated hearing test is, at least initially, made available only through a qualified hearing health professional. The hearing health professional may offer the automated hearing test as a separate service or as part of a more comprehensive service, such as a full physical checkup that patients can obtain annually. Since the test requires little or no intervention, the hearing health professional does not have to spend much time administering the test. As a result, he will have more time for each patient and/or be able to treat more patients. Moreover, since the automated hearing test facilitates early detection of hearing loss, the treatment needed may be less severe than if the hearing loss had been detected later.

Referring now to FIG. 1, a system 100 for providing automated hearing tests according to some embodiments of the invention is shown. The system 100 has three main components, namely, a computer 102, and a display screen 104, and at least one transducer 106. Other components of the system 100 that may be present include a tympanometer, keyboard, mouse, printer, paging system, and the like (indicated generally at 108). The paging system may be any suitable paging technology that uses one or more pagers or other wireless mobile devices 108 for alerting the operator. The mobile terminal 108 preferably can display text messages for informing the operator of the nature of the alert. Other types of paging system may also be used without departing from the scope of the invention (e.g., wired paging systems).

The computer 102 may be any suitable computer, from a desktop PC to a high-end workstation, as the particular type/model/brand of computer is not overly important to the practice of the invention. The display screen 104 may likewise be any suitable display screen, from a CRT to an LCD, as the particular type/model/brand of display screen is not overly significant for purposes of the present invention. In some embodiments, however, a touchscreen monitor may be easier to use than conventional CRT for LCD display screens in terms of the physical interaction between the patient and the automated hearing test.

As for the transducer 106, this component may be an ear insert, earphones, and the like for air conduction. For bone conduction, the transducer 106 may be a vibrator or other similar devices. In some cases, the transducer 106 may be mounted on a headset worn by the patient. Usually, a separate transducer is used for air conduction versus bone conduction and the transducers are swapped as need during the hearing test. Preferably, the bone conduction transducer is arranged in such a way as to allow testing of either ear without moving the transducer and without interfering with the air conduction transducer. In some embodiments, both the air conduction transducer and the bone conduction transducer are combined in a single unit. An example of such a combined unit is described in U.S. Provisional Patent Application entitled "System and Method for Conducting Multiple Diagnostic Hearing Tests," filed on Apr. 29, 2003, which is incorporated herein by reference.

Figure 2:
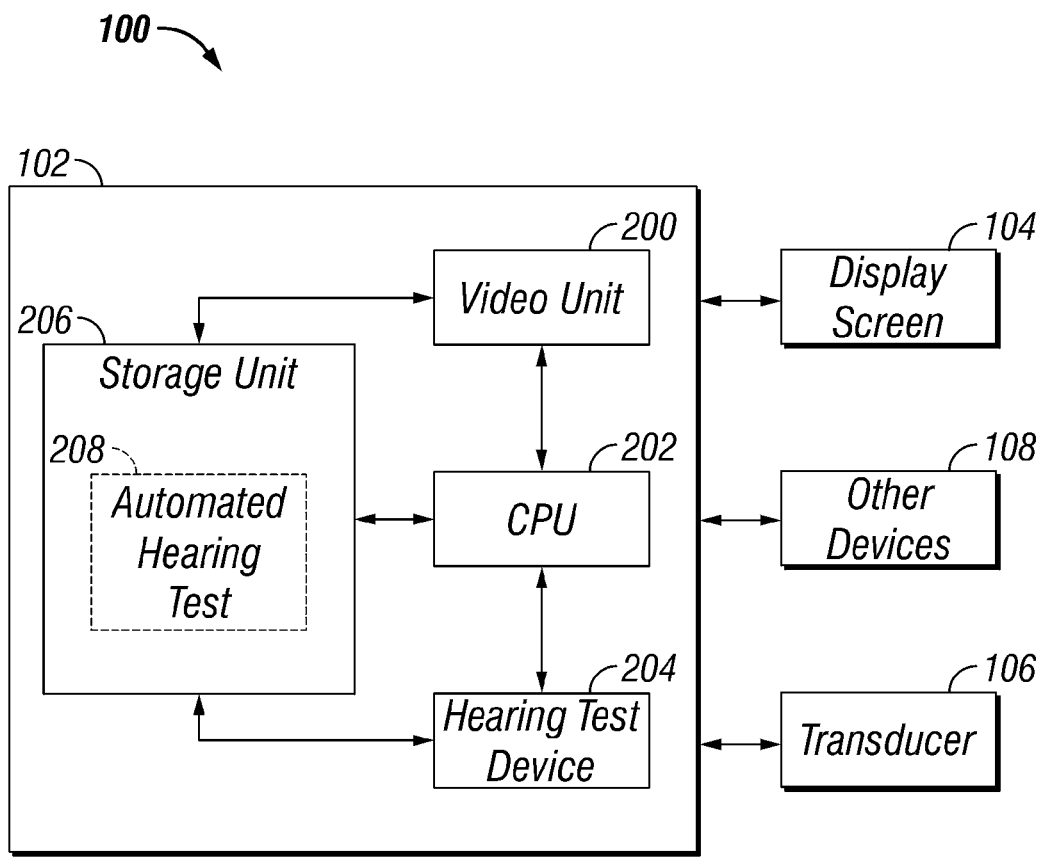
FIG. 2 illustrates a block diagram of the system for providing an automated hearing test according to embodiments of the invention.

FIG. 2 illustrates the system 100 in block diagram form. As can be seen, the computer 102 has a number of functional components, including a video unit 200, a central processing unit 202, a hearing test device 204, and a storage unit 206. These components are well known in the computer art and will therefore be described only briefly here. In general, the video unit 200 provides the video signals that are displayed as images on the display screen 104. In some embodiments, the video unit 200 may be any one of several commercially available video cards. The central processing unit 202 is responsible for the overall operation of the computer 102, including execution of the operating system and any software applications residing on the computer 102. In some embodiments, the central processing unit 202 may be any one of several commercially available microprocessors. The hearing test device 204 may comprise any or all of an audiometer, an otoacoustic emission test device, a tympanometer, a masking noise generator, or other hearing test devices. In some embodiments, the hearing test device 204 may be one or more electronic circuit boards within the computer 102 for performing the functionality of such test devices. Alternatively, the hearing test device 204 may be a separate unit that is external to the computer 102. The storage unit 206 provides long-term and temporary (i.e., caching) storage for the software and data that are used by the computer 102 and may include one or more of, for example, a hard drive, main memory, removable storage (e.g., CD-ROM, floppy disk), and the like.

In some embodiments, the storage unit 206 also stores the automated hearing test of the present invention, indicated at 208. More specifically, the storage unit 206 stores a computer-readable version of the automated hearing test 208 that can be executed by the computer 102. During execution, a portion of the automated hearing test 208 may be temporarily loaded from, for example, the hard disk and into the main memory components of the storage unit 206. In addition to the stand-alone arrangement, it is also possible to execute the automated hearing test 208 from a network. For example, the automated hearing test 208 may be stored on a server computer (not expressly shown) that is accessible to several client computers. This arrangement has an advantage in that updates to the automated hearing test 208 may be quickly and easily implemented. Other environments for executing the automated hearing test 208 may also be used without departing from the scope of the invention.

Figure 3:
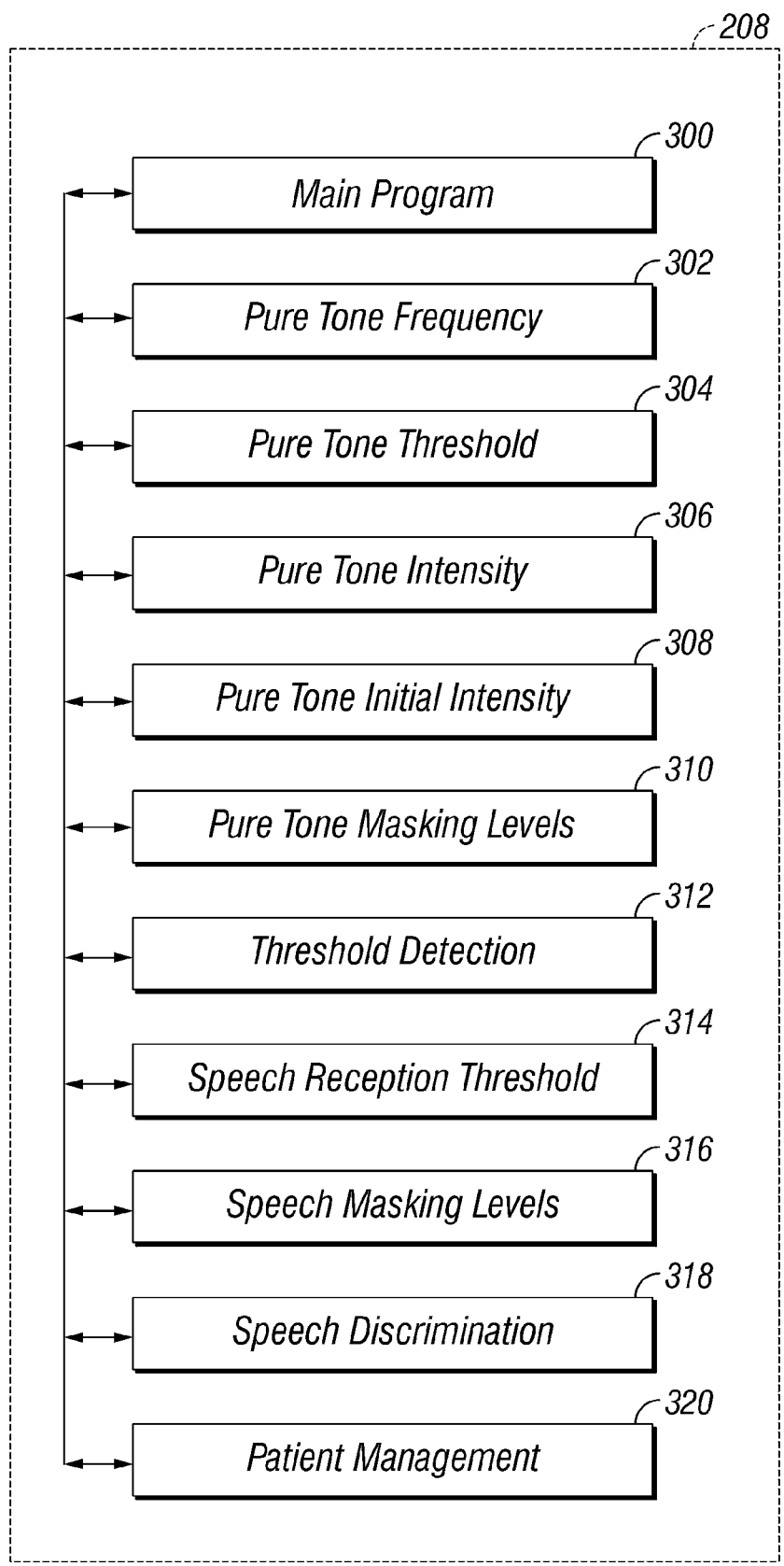
FIG. 3 illustrates the exemplary functional components of the automated hearing test according to embodiments of the invention.

The source code for the automated hearing test 208 may be written in any suitable programming language (e.g., C, C++, BASIC, Java). It has been found, however, that object oriented programming languages such as C++, Visual Basic and Java can result in a somewhat more efficient program. In addition, the automated hearing test 208 can be implemented using a number of different programming methodology (e.g., top-down, object oriented). The particular programming methodology as well as the particular programming language used are not overly important considerations for the practice of the invention. In one embodiment, the methodology of the automated hearing test 208 involves a plurality of individual modules or object class modules with subroutines, properties and functions that can be called to perform specific tasks. The modules or subroutines can be called from a main routine and from within other modules or subroutines. The subroutines can pass data to and from each other as well as to and from the main routine. FIG. 3 shows an example of this particular embodiment of the automated hearing test 208.

As can be seen in FIG. 3, the automated hearing test 208 includes a main program module 300 and a plurality of individual subroutines or class modules, including a pure tone frequency module 302, and a pure-tone threshold module 304. A pure tone intensity module 306, a pure tone initial intensity determination module 308, and a pure tone masking levels module 310 are also present. Other modules include a threshold detection module 312, a speech reception threshold module 314, a speech masking levels module 316, a speech discrimination module 318, and a patient management module 320. In evaluating the various modules, it should be emphasized that this particular combination of modules is exemplary only, and that one or more modules may be omitted or other modules may be added as needed. Furthermore, two or more modules may be combined into a single module, or a single module divided into several sub-modules as needed.

Functionally, the main program module controls the general sequence or flow of the hearing test 208. When specific functions or tasks need to be performed, the main program module calls the appropriate modules to perform the needed functions or tasks. For example, the main program module calls the pure tone frequency module in order to test the patient's ability to hear pure tone frequencies. Similarly, the speech reception threshold module is called in order to test the patient's ability to hear speech, and the speech discrimination module is called in order to test the patient's ability to discriminate between similar sounding words.

Each of the modules can also call other modules when specific functions or tasks need to be performed. For example, while the pure tone frequency module controls which pure tone frequencies will be tested and in what sequence, the actual threshold testing is performed by one or several other modules. Thus, after being called by the main program module, the pure tone frequency module can call, for example, the pure tone intensity module in order to obtain the patient's threshold intensity for a given frequency. The pure tone intensity module, in turn, calls the pure tone initial intensity determination module in order to determine the initial intensity level at which to begin testing. The pure tone intensity module also calls the pure tone masking levels module in order to determine the amount of masking that should be used with a given frequency. Finally, the pure tone intensity module calls the threshold detection module in order to establish whether a threshold intensity has been reached. The threshold detection module can also be called by the speech reception threshold module for the same purpose. The speech reception threshold module further calls the speech masking levels module in order to determine the amount of masking to be used during the speech reception threshold test. FIGS. 4-13 illustrate one exemplary implementation out of several possible implementations for each of the modules 302-320.

A key design feature of the automated hearing test is the ability to share data between all the modules that are called. For example, data acquired by the pure tone frequency module during the pure tone frequency test may be shared with the speech reception threshold module during the speech reception threshold test. Similarly, data acquired during one iteration of a module may be shared with another iteration of the same module. This type of data sharing arrangement results in a more efficient and more accurate test overall. Where no data exists to be shared, the modules may use rules of thumb type data or best-guest type data.

Figure 4:
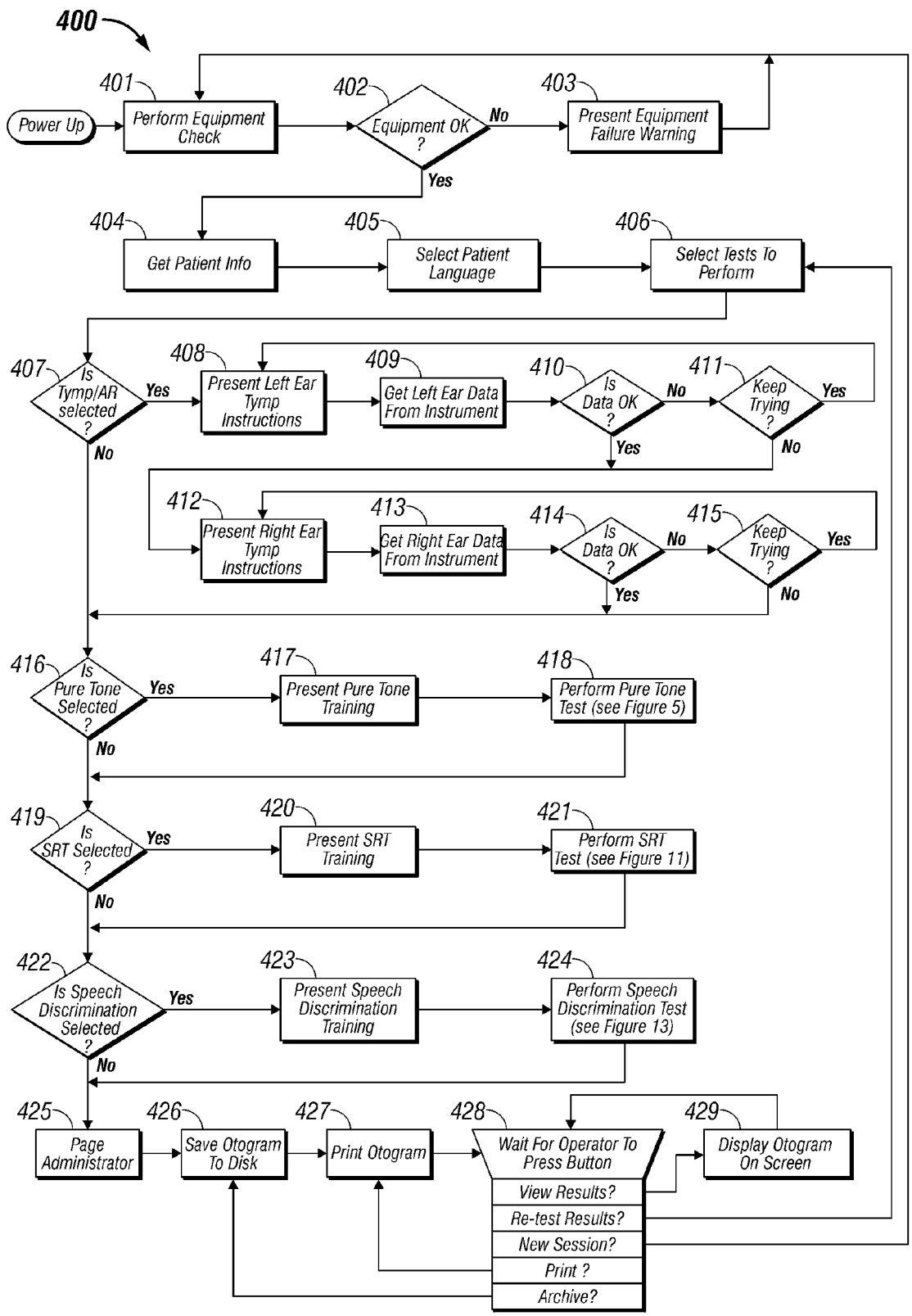
FIG. 4 illustrates an exemplary flowchart for a main program module according to embodiments of the invention.

Referring now to FIG. 4, a flowchart 400 illustrates the operation of the main program module according to some embodiments of the invention. As mentioned above, the main program module controls the general sequence or flow of the automated hearing test 208. The main program module allows the patient to select which tests are to be performed, then controls when and how various subroutines or modules are called to carry out the selected tests. After initial power up, the main program module performs an equipment check at step 401 to ensure all components (e.g., transducers, audiometer, etc.) of the system are functioning properly. Such a check may involve, for example, comparing the initial calibration data of the equipment with current measurements. In some embodiments, the various components of the equipment may be pre-calibrated together as a unit during manufacture or assembly. The calibration data may then be stored in a storage medium that is connected or attached to or sent together with the equipment. A determination is made at step 402 as to whether the equipment check passed, that is, whether the equipment is within a predetermined percentage of the initial calibration data. If the equipment check fails, then the main program module issues an equipment failure warning at step 403 and returns to the first step 401 to re-check the equipment.

If the equipment check passes, then the main program module proceeds to obtain the patient's information at step 404. This can be done, for example, by prompting the patient to manually enter his information (e.g., name, address, date of birth, etc.), or by loading the information from a previously stored patient file. Here, as throughout the description, manual prompting may be done visually by displaying the instructions as text on the display screen 104, or by audio instructions via the transducer 106, or by a combination of both in a multimedia approach. At step 405, the main program module obtains the patient's preferred language (e.g., English, Spanish, French, etc.), again, by prompting the patient, or by loading the selection from a previously stored file. At step 406, the main program module allows the patient to select one of several tests to be performed, including a tympanogram/acoustic reflex test, a pure tone test, a speech reception threshold test, and a speech discrimination test.

After the above selection, the main program module makes a determination as to whether the tympanogram/acoustic reflex test was selected at step 407. The purpose of this test is to check the acoustic admittance of the ear and is usually conducted by an operator of a tympanometer (indicated generally at 108). The tympanometer may be any suitable tympanometer that can be connected to and communicate with the computer 102. Most commercially available tympanometers have a serial, parallel, or other data port that can be used to transfer data to and from the computer 102. If the tympanogram/acoustic reflex test was selected, then at step 408, the main program module presents the operator with the left ear instructions (e.g., insert tympanometer, start test). At step 409, the main program module obtains the left ear data from the tympanometer. The main program module thereafter prompts the operator at step 410 to indicate whether the data is acceptable. If the operator indicates the data is not acceptable, the main program module asks the operator at step 411 whether to keep trying to obtain a tympanogram for the left ear. If the operator decides to keep trying, then the main program module repeats the process for the left ear starting at step 408. On the other hand, if the operator decides not to keep trying, or that the data is acceptable, then the main program module runs through the same process for the right ear at steps 412, 413, 414, and 415.

In some embodiments, instead of the operator performing the tympanogram/acoustic reflex test, the automated hearing test 208 may control the tympanometer so that the test is performed automatically. In these embodiments, the tympanometer may be a separate unit, or it may be a part of the functionality provided by the hearing test device 204. The main program module may then be configured to provide instructions to the patient on how to insert the probes for the tympanogram/acoustic reflex test. The probes may be standard probes used for such tests, or they be combination probes similar to the one described in U.S. Provisional Patent Application entitled "System and Method for Conducting Multiple Diagnostic Hearing Tests," mentioned above. The main program module then controls the operation of the tympanometer to initiate the test and acquires the resulting data. A similar arrangement may be used for other hearing related tests.

If the tympanogram/acoustic reflex test was not selected step 407, then the main program module proceeds to step 416, where it checks whether the pure tone test was selected. The purpose of this test is to assess what loss has occurred in the patient's ability to hear pure tones (e.g., a single frequency or a very narrow band of frequencies). The data obtained during the pure tone frequency test can then be used for the other tests. If the pure tone test was not selected, the program module proceeds to step 419. If the pure tone test was selected, the main program module thereafter presents instructions to the patient at step 417 on how to perform the test (e.g., what to expect, when to respond, how to respond, etc.). At step 418, the main program module calls the pure tone frequency module to perform the pure tone test, the details of which will be described below. The main program module thereafter proceeds to step 419 for the speech reception threshold test.

At step 419, a determination is made as to whether the speech reception threshold tests was selected. The purpose of this test is to assess what loss has occurred in the patient's ability to hear speech. If the speech reception threshold test was not selected, then the main program module proceeds directly to step 422 for the speech discrimination test. If the speech reception threshold test was selected, then the main program module presents instructions to the patient on how to perform the test at step 420 (e.g., what to expect, when to respond, how to respond, etc.). The main program module thereafter calls the speech reception threshold module to perform the speech reception threshold tests at step 421, the details of which will be described below. The main program module then proceeds to step 422 for the speech discrimination test.

At step 422, a determination is made as to whether the speech discrimination test was selected. The purpose of this test is to assess what loss has occurred in the patient's ability to discriminate between similar sounding words. If the speech discrimination test was not selected, then the main program module proceeds directly to step 425 to conclude the test session. Otherwise, the main program module presents instructions to the patient on how to perform the test at step 423 (e.g., what to expect, when to respond, how to respond, etc.). The main program module thereafter performs the speech discrimination tests at step 424, the details of which, again, will be described with respect to FIG. 4 below. The main program module then proceeds to step 425 to conclude the test session.

At step 425, the main program module alerts the operator that the patient has completed his hearing test, for example, by causing the operator to be paged. In some embodiments, the main program module also pages the operator if the patient does not complete the hearing test within a reasonable amount of time, for example, one hour. If the patient has not completed the hearing test within the given time, then that may indicate the patient is having some difficulty progressing through the test. The operator may also be paged by the patient, for example, by pressing an onscreen button if he needs assistance. Once completed, the main program module saves the data acquired from the test, for example, by storing the data onto a disk of the storage unit 206 at step 426. At step 427, the main program module generates and prints a standardized report based on the test data from the just concluded test session.

At step 428, the main program module offers the operator a number of options, including the option to view the results, repeat the test, begin a new session, print the test data, and archive the results. The main program module thereafter waits for the operator to make a selection. If the operator chooses to view the results, the main program module displays the test data on the display screen 104 at step 429, and returns to the previous step. If the operator chooses to rerun the hearing test, the main program module returns to step 406 and prompts the operator to select the tests to be rerun. If, on the other hand, the operator chooses to begin a brand new session, the main program module returns to the very first step 401. If the operator chooses to print the test results, then the main program module returns to step 427 and prints the results. If the operator chooses to archive the results, then the main program module returns to step 426 and saves the result to disk.

Figure 5:
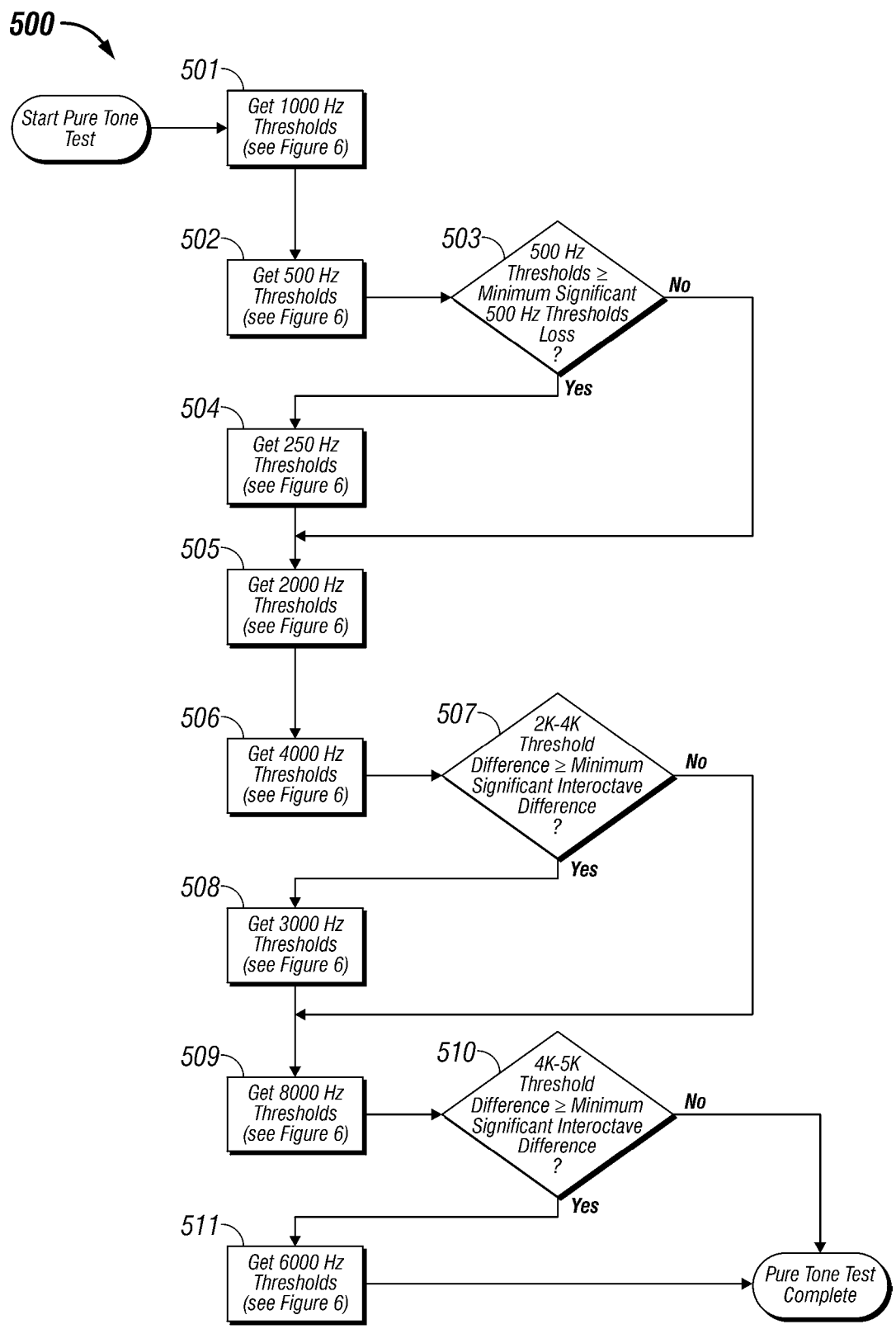
FIG. 5 illustrates an exemplary flowchart for a pure tone frequency module according to embodiments of the invention.

Referring now to FIG. 5, a flowchart 500 illustrates an exemplary implementation of the pure tone frequency module according to embodiments of the invention. The pure tone frequency module controls which pure tone frequencies are tested and in which sequence. As will be described below, a key design feature of the pure tone frequency module is its ability to determine whether certain frequencies need to be tested and to bypass the ones that do not need testing. This type of frequency selection process is very similar to the process that a hearing health professional would go through during a manually administered test and can result in a shorter and more efficient test overall.

At the first step 501, the pure tone frequency module obtains the threshold intensity for the first pure tone, which is about 1000 Hz in this embodiment. The threshold intensity is defined as the lowest intensity, rounded to the nearest 5 dB, at which the tone is audible to the patient at least 50% of the time. The pure tone frequency module obtains the threshold intensity by calling the pure tone threshold module and passing to it the frequency to be tested. The pure tone threshold module performs the pure tone threshold test (described below) and returns the results to the pure tone frequency module. At the second step 502, the pure tone frequency module obtains the threshold intensity for the second pure tone, which is about 500 Hz in this embodiment, by again calling the pure tone threshold module and passing the second pure tone information to it.

At the next step 503, the pure tone frequency module determines whether it needs to test below the 500 Hz level. This step is an optional step that is intended to reduce test time by skipping the lower frequencies if the results of lower frequency testing would not significantly add to the diagnostic information included in the hearing test report. The pure tone frequency module makes the determination by comparing the patient's threshold intensity at 500 Hz to the minimum significant 500 Hz threshold. The minimum significant 500 Hz threshold, according to some audiologists, is between 10 dB and 30 dB. If the patient's threshold intensity at 500 Hz is greater than or equal to the minimum significant 500 Hz threshold, then the pure tone frequency module proceeds to obtain the threshold intensity at a lower frequency, which is about 250 Hz in this embodiment at step 504. If the patient's 500 Hz threshold intensity is less than the minimum significant 500 Hz threshold, then there is less of a need to test at lower frequencies and time can be saved by skipping these frequencies. This demonstrates the advantage of starting the pure tone test at 1000 Hz rather than at the lowest frequency in the audible spectrum, since it is not always necessary to tests at the lowest frequencies. In some embodiments, however, the pure tone frequency module may test the lower frequencies anyway, or it may start at the lowest frequency in order to be as thorough as possible.

Next, the pure tone frequency module proceeds to obtain the threshold intensity at, for example, 2000 Hz (step 505) and at 4000 Hz (step 506), by again calling the pure tone threshold module and passing the frequency information to it. The pure tone frequency module may thereafter implement another optional time-saving measure at step 507 by determining whether the difference between the 2000 Hz and 4000 Hz thresholds is greater than a minimum significant interoctave difference. This minimum significant interoctave difference is considered by some audiologist to be about 20 dB. If the difference between the 2000 Hz and 4000 Hz thresholds is greater than or equal to the minimum significant interoctave difference, then the pure tone frequency module proceeds at step 508 to obtain the threshold intensity at 3000 Hz. Otherwise, the pure tone frequency module proceeds to step 509 to obtain the threshold intensity at, for example, 8000 Hz. At this point, the pure tone frequency module may implement another optional time-saving measure at step 510 by determining whether the difference between the 4000 Hz and 8000 Hz thresholds is greater than or equal to the minimum significant interoctave difference. If it is, then the pure tone frequency module proceeds at step 511 to obtain the threshold intensity at an intermediate frequency, for example, 3000 Hz. Otherwise, the pure tone frequency module concludes the procedure and returns the results to the main program module.

While the exemplary implementation of the pure tone frequency module described above started the pure tone testing at 1000 Hz, a person having ordinary skill in the art will recognize that other starting points may be used without departing from the scope of the invention. For example, the pure tone frequency module could start the testing at 8000 Hz and work down to the lower frequencies to obtain essentially similar results. Also, the pure tone frequency module may test frequencies above 8000 Hz, below 250 Hz, or at other interoctave frequencies not mentioned above without departing from the scope of the invention.

Figure 6:
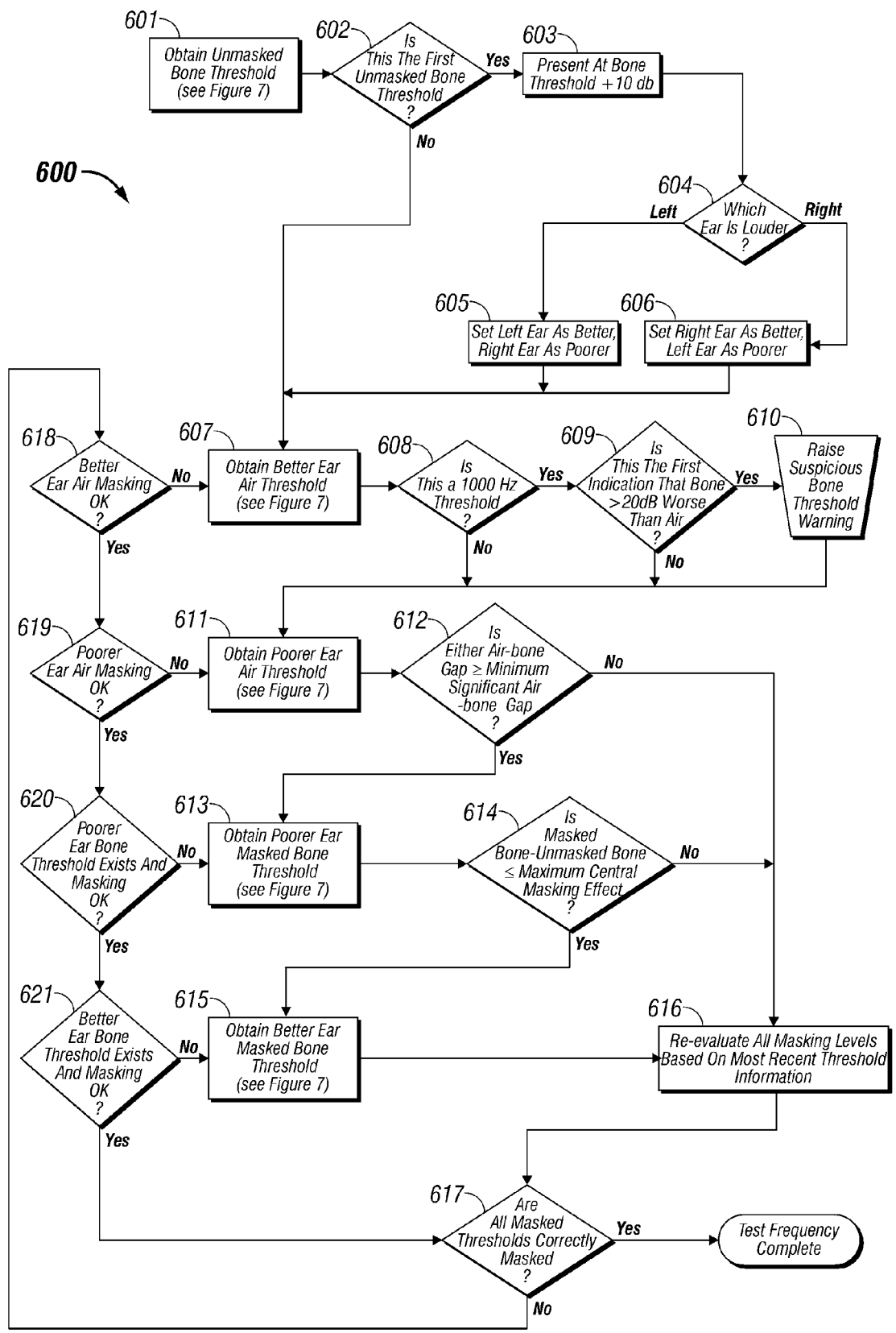
FIG. 6 illustrates an exemplary flowchart for a pure tone threshold module according to embodiments of the invention.

Turning now to FIG. 6, a flowchart 600 illustrates an exemplary implementation of the pure tone threshold module according to some embodiments of the invention. The pure tone threshold has the responsibility of coordinating the various tasks required to determine a threshold intensity for each pure tone frequency tested. For each pure tone frequency, the pure tone threshold module first obtains an unmasked bone threshold at step 601 by calling the pure tone intensity module (described below). The pure tone threshold module thereafter uses the unmasked bone threshold to determine whether the left ear or the right ear is louder, provided this determination has not already been made in a previous iteration. If it turns out that the louder ear determination has already been made, then the pure tone threshold module can skip this determination in the current iteration.

Thus, at step 602, the pure tone threshold module determines whether the unmasked bone threshold just obtained is the first unmasked bone threshold. If it is not, then that means the louder ear determination has already been made in a previous iteration, and the pure tone threshold module may proceed directly to the better ear air threshold test at step 607. If the unmasked bone threshold just obtained is the first unmasked bone threshold, then at step 603, the pure tone threshold module presents the frequency being tested to the patient using an intensity level roughly equal to the unmasked bone threshold plus a margin (e.g., 10 dB). The patient is then prompted at step 604 to indicate which ear can hear the frequency louder. Based on the patient's response, either the left ear is marked as the better one (step 605) or the right ear is marked as the better one (step 606). Note that this step is an optimization step and, if omitted, might make the test a little longer, but would not alter the end results.

At step 607, for whichever ear was denoted as the better ear, the pure tone threshold module obtains an air threshold for that ear by again calling the pure tone intensity module. The pure tone intensity module obtains an air threshold for the ear being tested and returns the results to the pure tone threshold module. The pure tone threshold module thereafter determines at step 608 whether the frequency being tested is the first frequency, which is 1000 Hz in this embodiment. If it is not, the pure tone threshold module proceeds to step 611 to obtain the air threshold for the other, poorer ear. On the other hand, if the frequency being tested is the first frequency, then at step 609, the pure tone threshold module determines whether the unmasked bone threshold is more than 20 dB worse than the air threshold just obtained. If it is not, the pure tone threshold module again proceeds to step 611. If the unmasked bone threshold is more than 20 dB worse than the air threshold just obtained, the pure tone threshold module raises a suspicious bone threshold warning at step 610. In some embodiments, the pure tone threshold module also alerts the operator, as this is usually an indication that the bone conduction transducer is disconnected, not on the patient, or has otherwise failed. The pure tone threshold module thereafter proceeds to step 611.

At step 611, the pure tone threshold module again calls the pure tone intensity module to obtain the air threshold for the poorer ear. At step 612, the pure tone threshold module determines whether the air-bone gap for either ear is greater than or equal to a minimum significant air-bone gap, which might indicate that a masked bone threshold is needed to establish the bone conduction of each ear. The minimum significant air-bone gap is about 10 dB according to some audiologists. Most people with normal hearing will have an air-bone gap that is smaller than this and, therefore, a masked bone threshold will not be needed and the pure tone threshold module can proceed directly to step 616.

If, however, the air-bone gap for either ear is greater than or equal to the minimum significant air-bone gap, then the pure tone threshold module proceeds to obtain masked bone thresholds, beginning with the poorer ear at step 613 (by calling the pure tone intensity module). The pure tone threshold module thereafter determines whether the masked bone and unmasked bone difference for that ear is less than or equal to a maximum central masking effect. The central masking effect is a measure of the level of masking noise introduced at the contralateral ear that can influence the audibility of tones at the ipsilateral ear. The maximum central masking effect is considered by some audiologist to be about 20 dB. If the poorer ear masked bone threshold is worse than the unmasked bone threshold by more than the central masking affect, one can safely assume that the unmasked bone threshold pertains to the better ear, and a separate threshold is not necessary. If, however, the poorer ear masked bone versus unmasked bone difference is less than or equal to the maximum central masking effect, then the pure tone threshold module proceeds to obtain the better ear masked bone threshold at step 615.

Note that steps 612 and 614 are optional time saving measures, since in most people with normal hearing, the pure tone threshold module will proceed directly to step 616 from these steps. At step 616, the pure tone threshold module reevaluates the masking levels used for each threshold obtained at steps 607, 611, 613, and 615 (if available) based on the most recent threshold information for the frequency being tested. It is possible that an early masked threshold was obtained with insufficient masking, since any conductive loss that may be present in the masked (non-test) ear would not be known ahead of time. For this reason, the masking level used for all thresholds at the frequency being tested are reevaluated after each new threshold is obtained in order ensure use of the most recent threshold information in determining appropriate masking levels. Reevaluation involves calculating the minimum masking level (described in more detail with respect to FIG. 9) using the most recent thresholds for the frequency being tested. If the newly calculated minimum masking level and the level used to obtain the threshold are different by more than a predetermined amount, then the threshold that was obtained may not be correct.

At step 617, the pure tone threshold module determines whether all masked thresholds have been correctly masked from the results of step 616. If they have, the pure tone threshold module concludes its procedure for the frequency being tested and returns the results to the pure tone frequency module. Otherwise, the pure tone threshold module determines whether the better ear air masking (step 618) and poorer ear air masking (step 619) were correct. If the air masking for either ear was incorrect, the pure tone threshold module repeats the air threshold procedure for the affected ear. The pure tone threshold module thereafter determines whether the bone threshold exists and bone masking was correct for the poorer ear (step 620) and the better ear (step 621). If the determination is no for either ear, the pure tone threshold module repeats the unmasked bone threshold procedure for the affected ear. The pure tone threshold module thereafter returns to step 617 to determine once again whether all mask thresholds were correctly masked for the frequency being tested. This process is repeated until all necessary thresholds are obtained with the proper masking levels.

Figure 7:
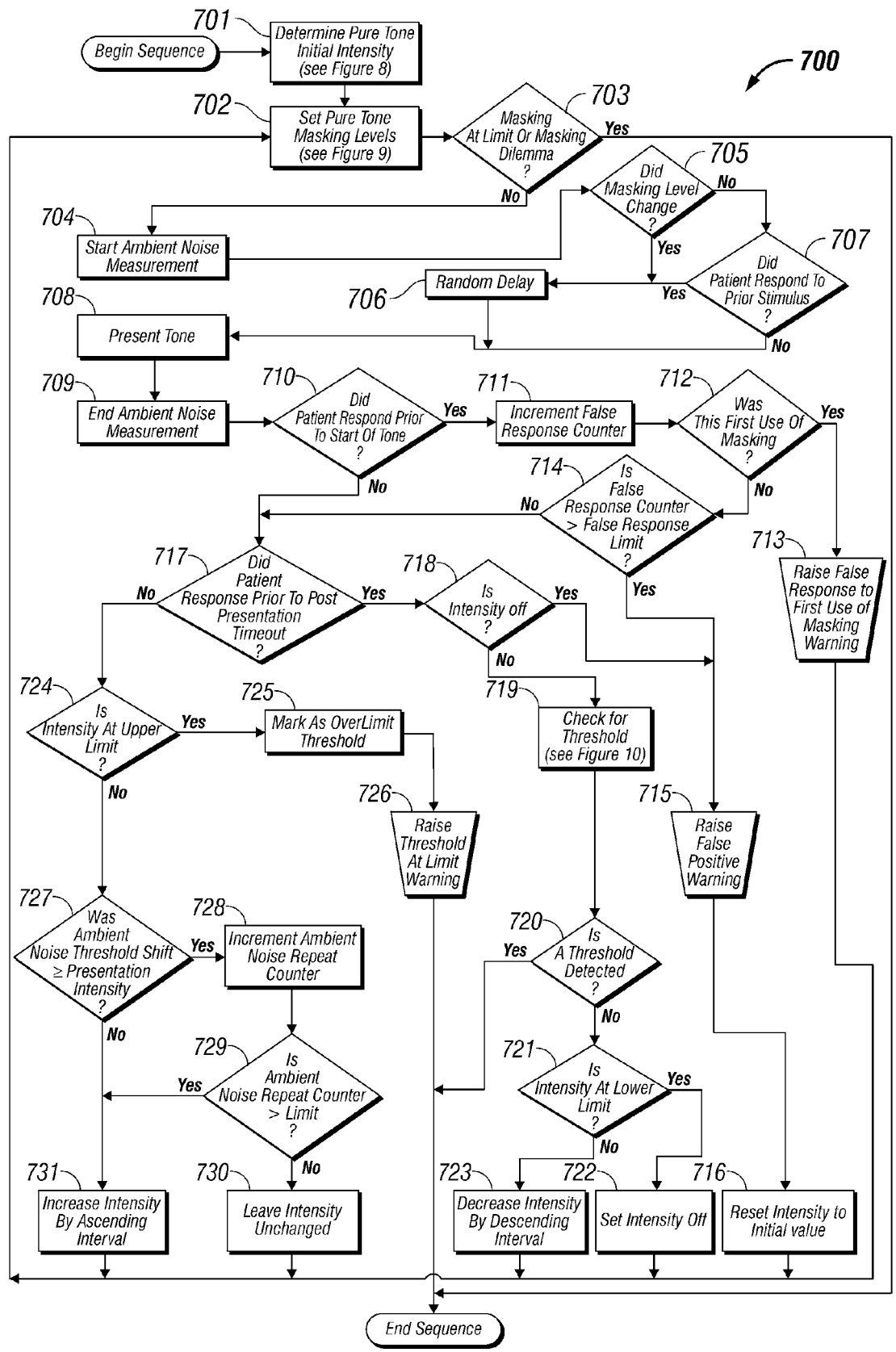
FIG. 7 illustrates an exemplary flowchart for a pure tone intensity module according to embodiments of the invention.

FIG. 7 illustrates a flow chart 700 of an exemplary implementation of the pure tone intensity module according to some embodiments of the invention. As mentioned above, the pure tone intensity module is called by the pure tone threshold module in order to determine an individual threshold intensity for the pure tone frequency being tested. The pure tone intensity module presents the frequency being tested using a series of different intensity levels and checking each level to see if it is at the patient's hearing threshold for that frequency. For each frequency, the pure tone intensity module begins by first determining the intensity level that should be used to start the testing. The pure tone intensity module then sets the masking level for that intensity level, and for each subsequent intensity level as needed.

One key design feature of the pure tone intensity module is the detection of a false response. If the intensity level testing reaches the equipment lower limit and still no threshold has been found, then the patient may be guessing or trying to anticipate the tones. In some embodiments, the pure tone intensity module turns the intensity level off at this point and checks whether the patient heard a tone. If he did, then the patient is given a false response warning, since he could not have heard a tone with the intensity turned off.

Another key design feature of the pure tone intensity module is that it measures the level of ambient noise present during an ongoing test. This allows the automated hearing test of the present invention to compensate for the ambient noise. As a result, the automated hearing test can be performed without a quiet room or a sound isolation chamber. The ambient noise may be measured at regular intervals, or at various predetermined points throughout the test. In some embodiments, the ambient noise may be measured at the moment each intensity level is used. In this way, real time analysis of the ambient noise is performed for each intensity level and can be compensated for as needed.

To determine the starting intensity level, the pure tone intensity module calls the pure tone initial intensity determination module (described below) at step 701. It also calls the set pure tone masking levels module at step 702 to determine the amount of masking for that intensity level. At step 703, the pure tone intensity module determines whether there is a problem with the masking level returned by the set pure tone masking levels module. A masking problem may result from equipment limitations (i.e., the masking level is beyond the limitations of the audiometer or the transducer), or the problem may be due to a masking dilemma. A masking dilemma occurs when the minimum masking level required at the non-test ear also masks the test ear due to crossover, causing the threshold levels in the test ear to be shifted. When such masking problems occur, the pure tone intensity module simply concludes its procedure for the frequency being tested and returns to the pure tone threshold module. In some embodiments, however, the pure tone intensity module may proceed anyway with unmasked thresholds in the case of a masking dilemma.

If there is no masking problem, then the pure tone intensity module proceeds with the testing by starting the ambient noise measurement at step 704. The ambient noise may be measured using any microphones suitable for the task, such as those described in U.S. Provisional Patent Application entitled "System and Method for Conducting Multiple Diagnostic Hearing Tests" mentioned above. Preferably, one microphone is placed near each ear, but it is also possible to place the microphones at other locations. At step 705, the pure tone intensity module determines whether the current masking level is different from the previous iteration's masking level. This determination is important because a change in the masking level can sometimes clue the patient that a tone is about to be presented. If there has been a change in the masking level, then the pure tone intensity module introduces a random delay (e.g., 0.5 to 3 seconds) at step 706 before presenting the tone. On the other hand, if the masking level did not change, but the patient responded to a prior stimulus at step 707 (which could happen only on the second and subsequent iterations of this loop), the pure tone intensity module will still introduce a random delay before presenting the tone. If the patient did not respond to a prior stimulus, however, then the pure tone intensity module proceeds with presentation of the tone pulse train at step 708. The presentation of the tone pulse train lasts about two seconds in some embodiments, but may be adjusted longer or shorter as needed. In some embodiments, a non-pulsed tone or frequency modulated tone (warble) may be used in place of a pulsed tone.

At step 709, the pure tone intensity module concludes the ambient noise measurement. This measurement will then be used to compensate for the level of ambient noise if needed. The pure tone intensity module thereafter determines at step 710 whether the patient responded prior to the start of the tone presentation. Such a response may indicate the patient is guessing or trying to anticipate the presentation of the tone. When this happens, the pure tone intensity module increments a false response counter at step 711, and determines whether the current masking is the first time masking is used for the frequency under test at step 712. If it is, then the false response may have been due to the patient not being ready for the sudden introduction of the masking noise. At this point, the pure tone intensity module internally raises a false response warning at step 713 to the patient, and returns to the set pure tone masking levels step 702 so that the same tone presentation can be repeated.

If the current masking is not the first time masking is used for the frequency under test (step 712), then the pure tone intensity module determines at step 714 whether the false response counter in step 711 has exceeded a predetermined limit. The predetermined limit is arbitrarily set at three false responses in some embodiments, but may be adjusted higher or lower as needed. If the false response counter has exceeded the predetermined limit, the pure tone intensity module raises a false response warning at step 715, which can be used to alert the user to respond only when they hear a tone. The pure tone intensity module thereafter resets the intensity level for the tone to the initial value at step 716, and returns to step 702 to begin the procedure again.

If the false response counter has not exceeded the predetermined limit, then the pure tone intensity module continues at step 717, where it determines whether the patient responded before expiration of a post presentation timeout period. The post presentation timeout period allows some time for the patient to respond even after the tone pulse train has stopped. This timeout period may be in the 0 to 2 second range; in this embodiment, the time period is set to about 0.5 seconds If the patient does respond before the post presentation timeout period expires, then the pure tone intensity module determines at step 718 whether that response occurred while the intensity level of the tone was off. The intensity level is turned off if the lower limit of the equipment has been reached and still no threshold has been found. This means the patient is probably trying to guess of anticipate the tones, as he could not have heard any tone while the intensity was turned off. The pure tone intensity module thereafter proceeds to issue the false response warning at step 715.

On the other hand, if the intensity level was not off, then the pure tone intensity module checks at step 719 to see if a threshold has been reached. The pure tone intensity module performs his task by calling the threshold detection module (described below). Afterwards, a determination is made at step 720 as to whether a threshold for the frequency being tested was found. If a threshold was found, the pure tone intensity module concludes its procedure for this frequency and returns the results to the pure tone threshold module. If a threshold was not found, then at step 721, the pure tone intensity module determines whether the current intensity level has reached the equipment's lower limit. If it has, then at step 722, the pure tone intensity module turns the intensity level off and returns to step 702 where the procedure will be repeated with no tone. If the current intensity level is not at the equipment's lower limit, then the pure tone intensity module decreases the intensity level at step 723 by a predetermined increment and returns to step 702 to repeat the procedure with the new intensity level.

Referring back to step 717, if the patient did not respond before expiration of the post presentation timeout period, meaning there was no patient response to the tone presentation, then the pure tone intensity module determines at step 724 whether the current intensity level has reached the equipment's upper limit. If it has, then the pure tone intensity module records that the patient's threshold intensity for the frequency being tested is above the equipment limit at step 725, and raises an internal warning at step 726. In some embodiments, the patient may be asked to press an on-screen button at this point to indicate that they have not dozed off during the test. If the button is pressed in a timely manner, then the test can continue; if not, the operator may be paged to wake the patient and help him get back to the task of responding to tones.

If the current intensity is not at the equipment's upper limit, then at step 727, the pure tone intensity module checks the level of ambient noise present. In some embodiments, the pure tone intensity module performs this check by determining whether the ambient noise threshold shift is greater than or equal to the current intensity level. An ambient noise threshold shift occurs when the ambient noise level is greater than the minimum level allowed by ANSI standards. The shift can be determined, as known to persons having ordinary skill in the art, by performing a frequency analysis of the ambient noise (measured at step 704) and comparing the frequency components to ANSI minimum requirements. If the shift is greater than or equal to the current intensity level, then at step 728, the pure tone intensity module increments an ambient noise repeat counter. The purpose of the counter is to ensure that any increase in the ambient noise is real and not just a temporary occurrence due to, for example, the patient coughing. Thus, the pure tone intensity module determines at step 729 whether the ambient noise repeat counter is greater than a predetermined limit, meaning the increased ambient noise was detected several times. The predetermined limit is arbitrarily set at three in some embodiments, but may be adjusted higher or lower as needed. In some embodiments the predetermined limit can be set to zero so that presentations are never repeated. If the ambient noise repeat counter is less than the predetermined limit, then at step 730, the pure time intensity module leaves the current intensity level as it is, and returns to step 702 to repeat the procedure with the intensity level unchanged. If the counter is greater than the predetermined limit, then at step 731, the pure tone intensity module increases the current intensity level by a predetermined increment, and returns to step 702 to repeat the procedure with the new intensity level.

Figure 8:
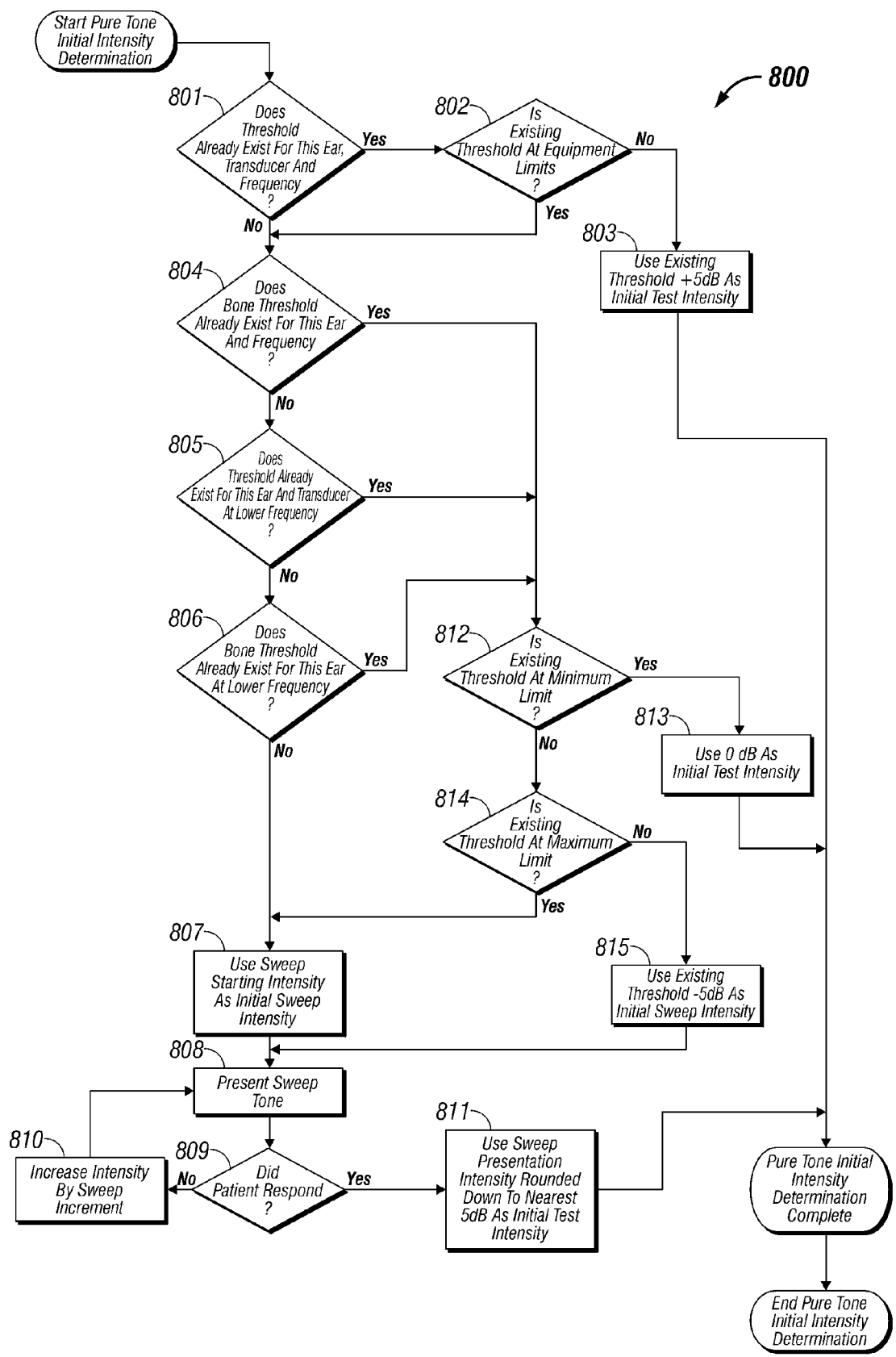
FIG. 8 illustrates an exemplary flowchart for a pure tone initial intensity module according to embodiments of the invention.

FIG. 8 illustrates an exemplary implementation of the pure tone initial intensity determination module, called by the pure tone intensity module to determine the initial testing intensity. In some embodiments, it is possible to simply start at one end of the available intensity spectrum and gradually progress to the other end. Such a process is inefficient, however, as some intensities may be unnecessarily tested. For example, if the patient's threshold intensity for the ear and frequency being tested is actually 20 dB, then it would be inefficient to start testing at 0 dB rather than, say, 10 dB. The pure tone initial intensity determination module therefore tries to choose a starting intensity that would eliminate at least some of the unnecessary intensities. It does this by identifying existing threshold intensities, if any, for the same ear, but taken from a different iteration of the module or a different session of hearing test. The pure tone initial intensity determination module then chooses a starting intensity level based on the existing threshold. If there are no existing thresholds, the pure tone initial intensity determination module uses an ascending intensity sweep algorithm to determine a starting intensity.

As can be seen from the exemplary flowchart 800, the first step is to determine whether a threshold intensity already exists for a particular transducer (e.g., bone or air conduction), frequency and ear being tested at step 801. The reason for this determination is some existing thresholds might need to be retested because of, for example, new information obtained about the opposite ear. The existing threshold may be from a previous iteration of the module or a previous session of the hearing test provided the data is not too old (e.g., less than six months). If one does exist, then the next step is to determine whether that existing threshold intensity is at the equipment's upper intensity limit at step 802. If a threshold intensity is not at either the low or high limit of the equipment, then the pure tone initial intensity determination module sets the initial tests intensity equal to the threshold intensity plus a predetermined margin at step 803. The predetermined margin is 5 dB in some embodiments, but may be adjusted higher or lower as needed. The pure tone initial intensity determination module thereafter concludes its procedure and returns the results to the pure tone intensity module.

If a threshold intensity does not already exist at step 801, or if the existing threshold intensity is at the equipment's upper or lower limit at step 802, the pure tone initial intensity determination module determines whether a bone threshold intensity exists for the frequency and the ear being tested at step 804. If the determination is no, the pure tone initial intensity determination module determines at step 805 whether a threshold intensity already exists for the ear being tested at a lower frequency. If the determination is again no, the pure tone intensity determination module determines at step 806 whether a bone threshold intensity already exists for the ear being tested at a lower frequency. If the determination is yet again no, then the pure tone initial intensity determination module proceeds to step 807, where it uses the sweep starting intensity as the initial sweep intensity for the ascending intensity sweep algorithm. In some embodiments, the sweep starting intensity is 20 dB, but may depend on the equipment being used. At step 808, the pure tone initial intensity determination module presents the pure tone frequency being tested at an intensity level equal to the initial sweep intensity, but with a shorter duration than a normal tone presentation. A determination is made at step 809 as to whether the patient responded to the tone presented. If he did not respond, then the intensity of the tone is increased by a predetermined increment at step 810, and the tone is presented again. If the patient did respond, then at step 811, the initial intensity is set equal to the intensity of the current tone rounded down to the nearest 5 dB. Using a shorter sweep pulse with rapid increases in intensity in the absence of patient responses allows a very rough approximation of threshold to be quickly determined. This approximation forms the starting point for more rigorous threshold determination. The pure tone initial intensity determination module thereafter concludes its procedure and returns the results to the pure tone intensity module.

If the determination made at any of steps 804, 805, and 806 is yes, then the pure tone initial intensity determination module proceeds to step 812, where it determines whether the existing threshold is at the equipment's lower intensity limit. If it is, then the pure tone initial intensity determination module sets the initial tests intensity to 0 dB at step 813 and returns the results to the pure tone intensity module. If the existing threshold is not at the equipment's lower intensity limit, then at step 814, a determination is made as to whether the existing threshold is at the equipment's upper intensity limit. If it is, the pure tone initial intensity module continues to step 807 and proceeds as described above. If it is not, the pure tone initial intensity determination module sets the sweep starting intensity equal to the existing threshold minus a predetermined margin (e.g., 5 dB) at step 815. The pure tone initial intensity determination module continues to step 808 and proceeds as described above.

Figure 9:
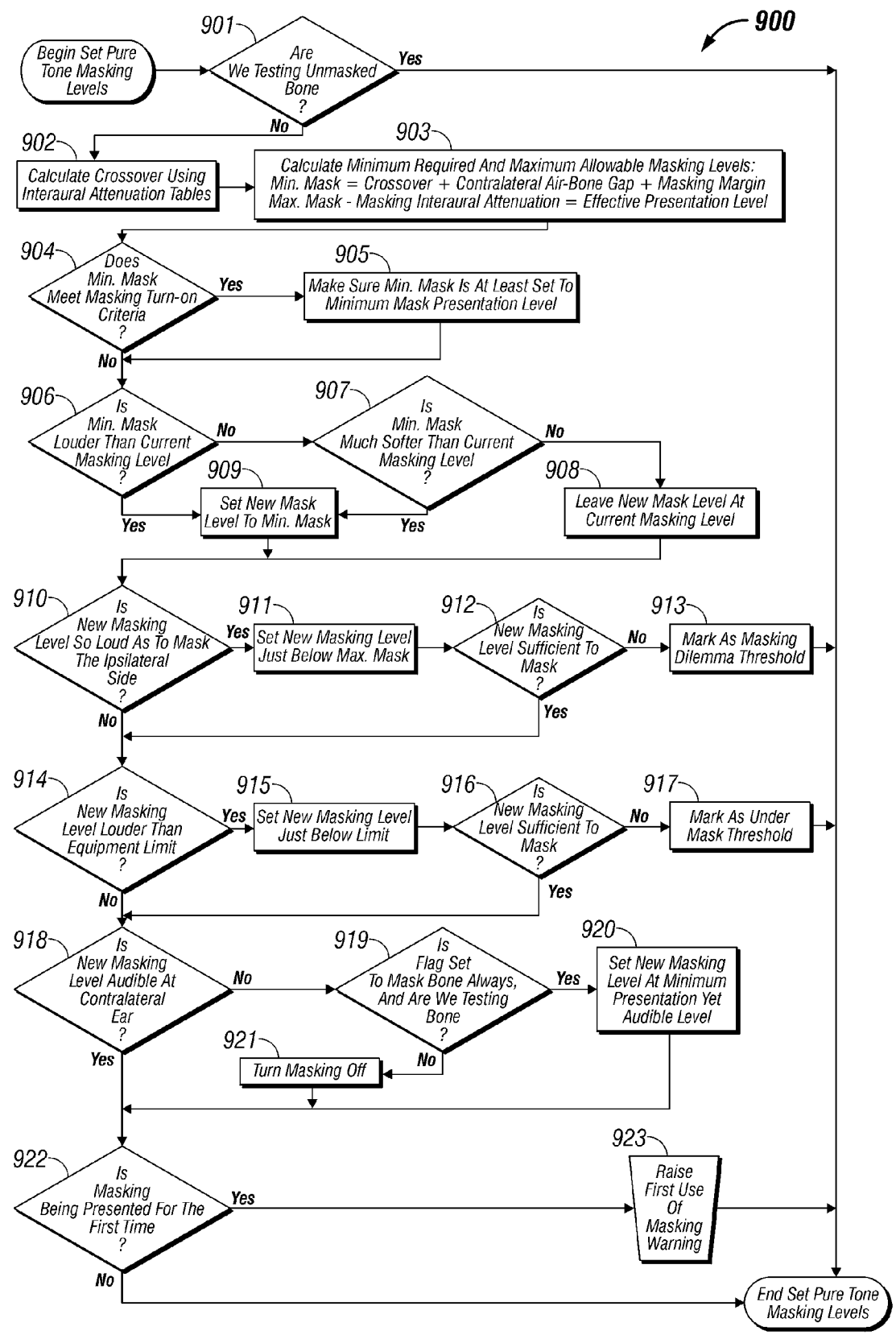
FIG. 9 illustrates an exemplary flowchart for a set pure tone masking levels module according to embodiments of the invention.

FIG. 9 illustrates a flowchart 900 for an exemplary implementation of the set pure tone masking levels module according to some embodiments of the invention. Masking prevents the non-test ear from hearing the tone presented in the test ear due to crossover. Crossover is a phenomenon in which sound presented in one ear propagates through the skull and stimulates the opposite ear. This phenomenon is frequency dependent, that is, certain frequencies propagate through the skull better than others. The phenomenon is also transducer dependent; for example, the crossover is different for insert earphones than for headphones at a given frequency. Masking introduces a narrow band signal in the non-test ear centered around the frequency being tested in order to "mask" the sound that has crossed over. It is important, however, to use the correct intensity level for the masking noise. Too little noise may be insufficient to mask the sound, while too much noise may have a reverse crossover effect (i.e., the masking noise crosses over and is audible in the test ear). Sometimes it is possible to arrive at the correct masking level by monitoring the shift in the threshold of the test ear for each masking level. A linear shift, for example, may indicate the threshold of the test ear is tracking the masking noise in the non-test ear, which may mean there is too much masking. This process, however, is not very efficient. Therefore, the purpose of the set pure tone masking levels module is to quickly determine approximately the right levels of masking for the frequency being tested.

The set pure tone masking levels module determines the appropriate amount of masking by first determining a minimum required amount of masking. This minimum masking level should be sufficient to overcome any loss in the non-test ear in addition to any crossover. It should be noted that, in general, a masking level that is somewhat higher than the minimum required is acceptable, but an insufficient amount of masking can lead to erroneous results. If it turns out that the minimum amount of masking required for the patient is very low (i.e., below a predefined turn-on criteria), then no masking is used, as it would have neutral or no benefit.

Otherwise, the set pure tone masking levels module sets the masking at a level that is a little higher than the minimum required. The reason for doing so is that a higher masking level makes it easier for the patient to distinguish the masking from a faint tone. Also, each change in the masking level may alert the patient to the tone presentation. Therefore, the set pure tone masking levels modules implements a hysteresis by setting the masking at a level that is a little higher than the minimum required. This allows multiple ascending tone presentations to be made before having to make adjustments to the masking level.

As can be seen from the flowchart 900, the first step is to determine whether unmasked bone is currently being tested at step 901 (see step 601 in FIG. 6). If it is, then there is no need to set a masking level, and the set pure tone masking levels module concludes its procedure and returns to the previous module. If unmasked bone is not being tested, then at step 902, the set pure tone masking levels module calculates the amount of crossover expected for the frequency being tested. In some embodiments, the crossover calculations are based on well known inter-aural attenuation tables, an example of which is shown in Table 1 below.

TABLE 1

| Attenuation | INTER-AURAL ATTENUATION | | | | | | | |
|---|---|---|---|---|---|---|---|---|
| | Frequency (Hz) | | | | | | | |
| (dB) | 250 | 500 | 1000 | 2000 | 3000 | 4000 | 6000 | 8000 |
| Min. | 44 | 54 | 57 | 55 | 56 | 61 | 56 | 51 |
| Max. | 58 | 65 | 66 | 72 | 72 | 85 | 76 | 69 |
| Mean | 51 | 59 | 61 | 61 | 68 | 70 | 65 | 57 |

Using the mean values from Table 1 above, the amount of attenuation expected for a 500 Hz tone is about 59 dB. Thus, at this frequency, a tone that has a presentation level of less than 59 dB would not produce any crossover and would not need to be masked. On the other hand, a tone that has a presentation level of, say, 65 dB, would produce about 6 dB of crossover that would need to be masked.

Once the crossover values have been calculated for the frequency being tested, the set pure tone masking levels module calculates at step 903 the minimum required masking level and the maximum allowable masking level for the frequency being tested. The minimum masking level, in general, is the lowest level of masking that can still mask any crossover in the non-test ear. In some embodiments, the minimum masking level is defined as a sum of the crossover plus the non-test ear air-bone gap. The crossover can be determined from the inter-aural attenuation tables as described above. The non-test ear air-bone gap, at least initially, is assumed to be 0 dB. In some embodiments, a margin of 5 dB may be added to the minimum masking level in order to ensure there is sufficient masking, although the masking margin may be adjusted higher or lower as needed. The maximum masking level is the level beyond which masking in the non-test ear will be heard in the test ear at a level sufficient to mask the test signal being presented. In some embodiments, the maximum masking level may be defined as that level which, when one subtracts the masking inter-aural attenuation, results in the effective presentation level. The effective presentation level is the intensity level of the tone as it is received at the inner ear. For air testing, the effective presentation level is the air conduction intensity level minus the air-bone gap. For bone testing, the effective presentation level is about equal to the bone conduction level.

At step 904, set pure tone masking levels module determines whether the minimum masking meets the masking turn-on criteria. The turn-on criteria is 0 dB in some embodiments, but may be adjusted higher as needed. If the turn-on criteria is met, then at step 905, the set air tone masking levels module makes sure that the minimum masking is at least set to the minimum masking presentation level. The minimum masking presentation level is 20 dB in some embodiments, but may be adjusted higher or lower as needed. If the turn-on criteria is not met, the set pure tone masking levels module determines at step 906 whether the minimum masking level is louder than the current masking level. If it is not, then the set pure tone masking levels module determines at step 907 whether the minimum masking level is much softer (e.g., about 25 dB) than the current masking level. If it is again not, then the set pure tone masking levels module makes no change to the current masking level at step 908. Note that steps 907 and 908 are optional and are intended to act as the hysteresis function to prevent small or insignificant changes from being made to the masking level. In general, the fewer changes that are made to the masking level, the better, since each change is distracting and can potentially alert the patient that a tone is about to be presented.

If the minimum masking level determined in step 903 is louder than the current masking level (step 906), or if the minimum masking level is much softer than the current masking level (step 907), then at step 909, the set pure tone masking level module sets the new masking level equal to the minimum masking level. At step 910, the set for tone masking levels module determines whether the new masking level is so loud as to mask the test ear. If it is, then the set pure tone masking levels module sets the new masking level just below the maximum masking level at step 911, and determines whether this new masking level provides a sufficient amount of masking at step 912, that is, whether the new masking level is greater than or equal to the minimum masking level calculated at step 903. If the new masking level is not loud enough, then the set pure tone masking levels module raises an indication that there is a masking dilemma at step 913.

On the other hand, if the new masking level is sufficiently loud, then at step 914, the set pure tone masking levels module determines whether the new masking level will be louder than the equipment's loudest level. If it is, then the set pure tone masking levels module sets the new masking level just below the equipment's limit at step 915. The set pure tone masking levels module thereafter determines at step 916 whether this new masking level is sufficient to mask. If it is not, then at step 917, the set pure tone masking levels module raises an indication that the resulting threshold will be undermasked. If it is, then the set pure tone masking levels module determines whether the new masking level is audible in the non-test (masked) ear at step 918. If the new masking level is not audible in the non-test ear, then in some embodiments, masking is simply turned off at this point.

In some embodiments, however, the operator is given the option of requiring masking to be on for all bone conduction testing. If that option is exercised (e.g., via an internal flag), then the set pure tone masking levels module determines at step 919 whether bone conduction is currently being tested, and whether masked bone conduction is required (i.e., the internal flag is set). If this determination is yes, then at step 920, the set pure tone masking levels module sets the new masking level equal to the minimum presentation level that is still audible, as determined by the greater of the minimum configurable masking intensity, the minimum mask turn-on level (e.g., 0 dB), and the air threshold for the non-test ear (where available). This allows the automated hearing test to obtain a masked bone threshold for the ear being tested even though the minimum calculated masking level would not have been heard by the patient.

If bone conduction is not currently being tested, or if masking is not required for all bone threshold tests, then masking may be turned off at step 921. Thereafter, the set pure tone masking levels module determines whether masking is being attempted for the first time at step 922. If it is, then the set pure tone masking levels module warns the patient that masking is about to begin at step 923. If it is not, as in the case when masking is turned off, the set pure tone masking levels module concludes its procedure and returns the results to the pure tone intensity module. In some embodiments, after step 921, the set pure tone masking levels module may proceed directly to the conclusion of the procedures.

Figure 10:
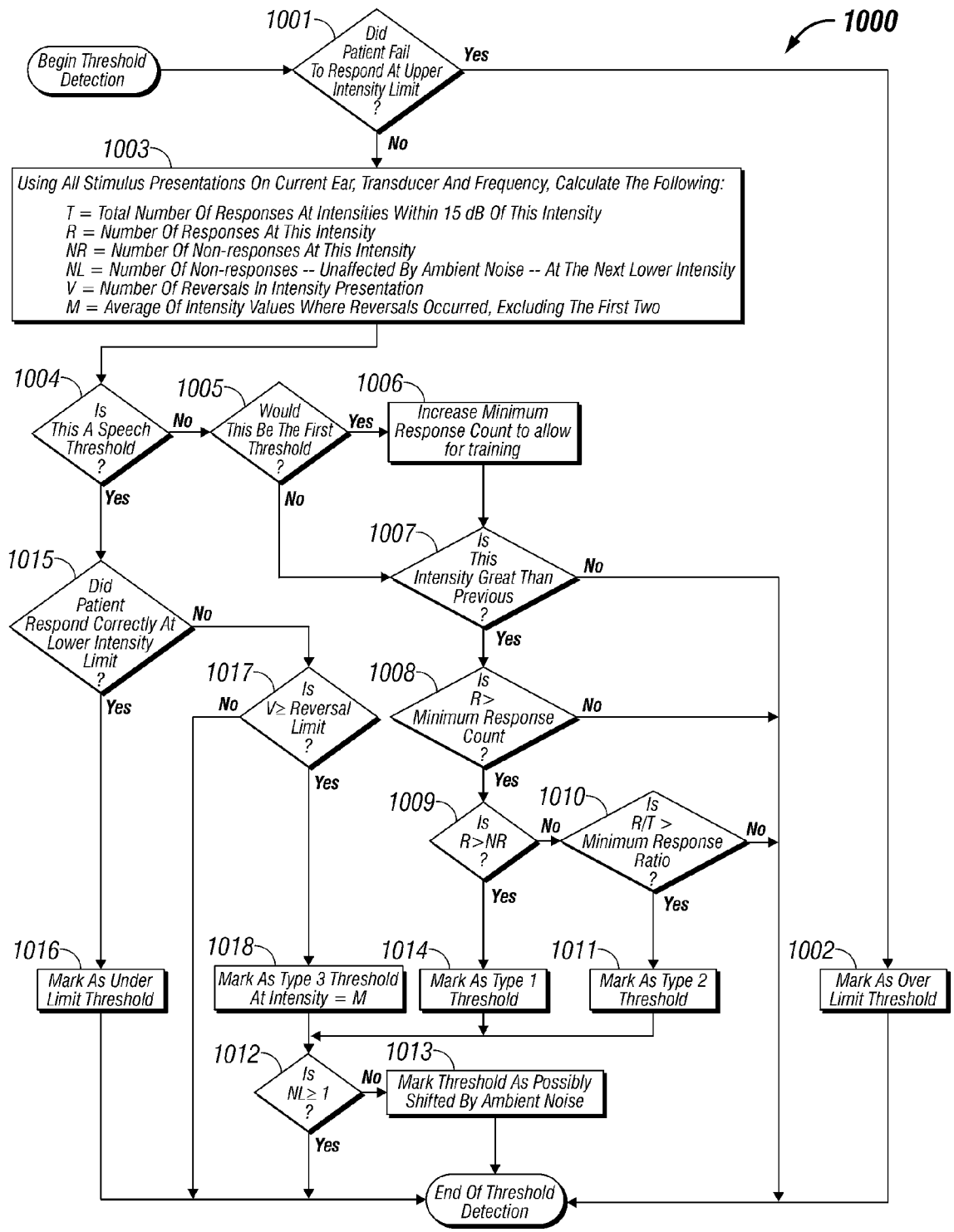
FIG. 10 illustrates an exemplary flowchart for a threshold detection module according to embodiments of the invention.

FIG. 10 illustrates a flowchart 1000 for an exemplary implementation of the threshold detection module according to some embodiments of the present invention. This module is the one called by the pure tone intensity module (FIG. 7) to determine whether a threshold intensity has been reached. The threshold detection module makes this determination by comparing the current intensity to a number of predetermined milestones or indicators. Depending on the comparisons, the threshold detection module records the threshold, if any, as a Type 1, 2, or 3 category threshold. These threshold types are arbitrarily assigned to indicate there are different ways that a threshold may be detected. In general, certain approaches to threshold determination may be optimal for speech thresholds, while other approaches are optimal for pure tone thresholds. The threshold detection module accommodates the different approaches by implementing more than one way to establish a threshold. Although only three threshold types are discussed, other threshold detection techniques may certainly be added to the threshold detection module as needed. Another key design feature of the threshold detection module is that it checks to make sure that the threshold reached was not significantly affected by any ambient noise that may have been present.

The first step that is performed by the threshold detection module is to determine whether the patient failed to respond at the equipment's upper intensity limit at step 1001. If he did, then the threshold detection module notes that the patient's threshold intensity for the frequency being tested is beyond the limit of the equipment at step 1002, and thereafter concludes its procedure. If the patient did respond at or below the equipment's upper intensity limit, then at step 1003, the threshold detection module proceeds to calculate several milestones or indicators, including: (T) total number of responses at intensities within 15 dB of the current intensity, (R) number of responses at the current intensity, (NR) number of non-responses at the current intensity, (NL) number of responses that are unaffected by ambient noise at the next lower intensity, (V) the number of reversals in the direction of progression of the intensity presentations, and (M) the average of the intensity values where reversals have occurred, excluding the first two values in some embodiments. It should be emphasized that these particular milestones or indicators are exemplary only, and that other milestones or indicators may also be used without departing from the scope of the invention.

After the milestones or indicators have been calculated, the threshold detection module in one embodiment proceeds to step 1004, where it determines whether the current threshold detection is for speech reception threshold (i.e., the module was called by the speech reception threshold module). If it is not, the threshold detection module determines whether the current threshold detection is the first threshold detection at step 1005. If it is the first threshold detection, then one embodiment of the threshold detection module increases the minimum response count to allow for training purposes at step 1006. For example, usually the minimum response count may be set equal to two, but may be equal to three or more for the first threshold detection to allow the patient to become familiar with the procedure.

If the current threshold detection is not the first threshold detection, the threshold detection module proceeds directly to step 1007 to determine whether the current intensity level is greater than the previous intensity level, i.e., greater than the intensity level used the last time the threshold detection module was called. If it is greater, then at step 1008, the threshold detection module determines whether the number of responses at the current intensity level exceeds the minimum response count. If it does exceed the minimum response count, then at step 1009, the threshold detection module determines whether the number of responses at the current intensity level (R) is greater than the number of non-responses at this intensity level (NR). If (R) is not greater than (NR), then at step 1010, the threshold detection module determines whether the ratio of the number of responses at the current intensity level (R) over the total number of responses at intensities within 15 dB of this intensity (T) is greater than the minimum response ratio. In some embodiments, the minimum response ratio is set to one-half, but may be adjusted higher or lower as needed. The ratio (R)/(T) can indicate whether the responses are being clustered or grouped together around a certain intensity level, which may indicate the patient has a threshold at that intensity level.

If (R)/(T) is greater than the minimum response ratio in step 1010, then the threshold detection module indicates that a threshold has been reached, and assigns it a Type 2 for internal usage at step 1011. The threshold detection module thereafter determines at step 1012 whether the number of non-responses that are unaffected by ambient noise at the next lower intensity level is greater than or equal to a minimum value. The minimum value may be one in some embodiments, but may be adjusted higher as needed. If (NL) is greater than or equal to the minimum value, then ambient noise was not a significant factor in the threshold detection, and the threshold detection module concludes its procedure and returns to the pure tone intensity module. Otherwise, if (NL) is less than the minimum value, then at step 1013, the threshold detection module marks the resulting threshold as possibly shifted by ambient noise.

If, on the other hand, (R) is greater than (NR) at step 1009, the threshold detection module indicates that a threshold has been reached at step 1014, and assigns it a Type 1 for internal use. The threshold detection module then proceeds to step 1012 for the affected by ambient noise check.

Furthermore, if the current intensity level is not greater than the previous intensity level (step 1007), or (R) is not greater than the minimum response counter (1008), or (R)/(T) is not greater than the minimum response ratio (step 1010), then there is no threshold detected, and the threshold detection module simply concludes its procedure.

If it turns out that the current threshold detection is for a speech threshold (step 1004), then at step 1015, the threshold detection module determines whether the patient responded correctly at the equipment's lower intensity limit. If he did, then at step 1016, the threshold detection module notes that the patient's threshold intensity is below the equipment's lower intensity limit. If the patient did not respond correctly at the lower intensity limit, then at step 1017, the threshold detection module determines whether the number of reversals (V) is greater than or equal to a reversal limit. In some embodiments, the reversal limit is four, but may be adjusted higher or lower as needed. If (V) is not greater than or equal to the reversal limit, then the current intensity is not a threshold, and the threshold detection module concludes its procedure. Otherwise, the threshold detection module notes that a threshold has been reached at an intensity level equal to the average of the intensity values where reversals have occurred (M) at step 1018, and assigns it a Type 3 for internal use. The threshold detection module then proceeds to step 1012 for the affected by ambient noise check.

Figure 11:
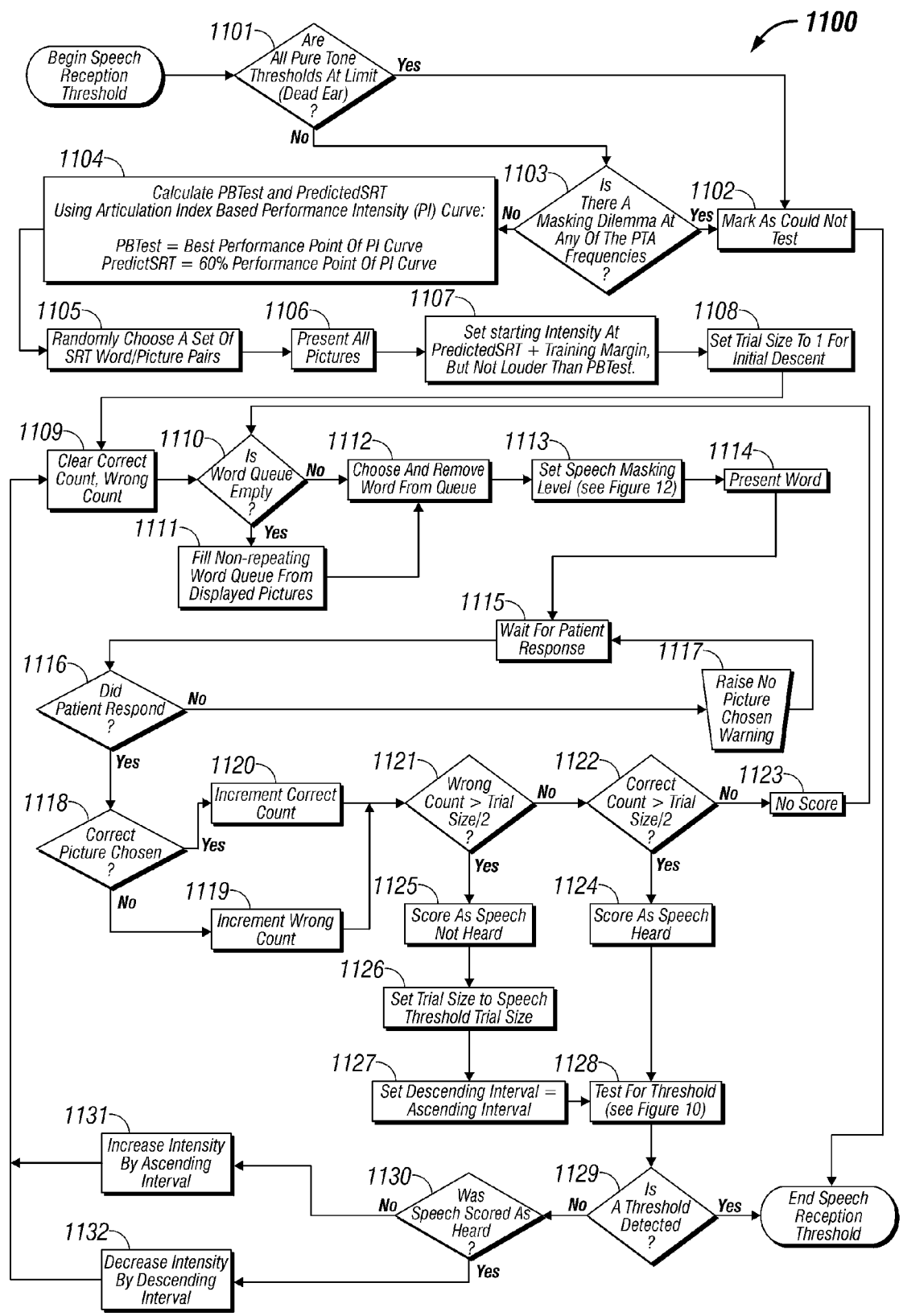
FIG. 11 illustrates an exemplary flowchart for a speech reception threshold module according to embodiments of the invention.

FIG. 11 illustrates a flowchart 1100 for an exemplary implementation of the speech reception threshold module according to some embodiments of the invention. The speech reception threshold module is called by the main program module to perform the speech reception threshold test. In some embodiments, the speech reception threshold module calculates a best performance intensity level and an expected performance intensity level according to a performance intensity (PI) curve. The PI curve is a prediction of the patient's performance at various intensity levels based on an Articulation Index (AI). The AI is a mathematical formula that is used to predict the word recognition ability of normal listeners given any combination of test material, frequency filter, level, and noise. For more information about AI and the PI curve, see "The articulation index in clinical diagnosis and hearing aid fitting," by Chris Halpin, PhD, Aaron Thornton, PhD, and Zezhang Hous, PhD, Current Opinion in Otolaryngology & Head and Neck Surgery, 4:325-334, 1996.

The speech reception threshold module then uses the best performance intensity level and the expected performance intensity level to control the intensity levels of the speech reception threshold test. Such an arrangement helps avoid having to start the speech reception threshold test at an intensity level that is too low or too high. If there is no existing data on the patient from which to calculate these intensity points, then the speech reception module starts with a fairly loud volume, for example, 60 dB, then quickly steps the intensity down until the patient can no longer hear the presentations. After that, the intensity levels are adjusted in smaller increments. If data exists, the speech reception threshold module sets the starting intensity level directly to the expected performance intensity level and increases or decreases it in small increments to reach a threshold intensity.

The speech reception threshold module then presents a set of randomly chosen pictures to the patient along with the words for the pictures. In some embodiments, the same set of randomly chosen pictures is used for the entire test, although it is possible to use more than one set. Preferably, the words that are used are compound words with two distinct syllables. For languages where no such words are used, appropriate substitutes may be made. The words are randomly presented one at a time to the patient with no emphasis on any syllable. The speech reception threshold module then waits for the patient to select the picture matching the word presented. For the first intensity level, a single response, whether correct or incorrect, initiates the threshold detection procedure. For each subsequent intensity level, two or more responses are needed, whether correct or incorrect, before threshold detection is initiated. In some embodiments, two consecutive wrong choices result in an incorrect answer, and two consecutive right choices result in a correct answer. Where there is one wrong choice followed by one right choice, the next choice determines whether the answer is correct or incorrect.

Referring now to FIG. 11, at the first step 1101, the speech reception threshold module determines whether all of the pure tone thresholds are at the upper limit of the equipment. If they are, then that means the ear being tested is not capable of hearing any tones (i.e., the ear is a dead ear). At this point, the speech reception threshold module simply notes that the ear could not be tested at step 1102. The speech reception threshold module thereafter concludes its procedure and returns to the calling module.

If the ear is not a dead ear, then at step 1103, the speech reception threshold module determines whether there is a masking dilemma at any of the pure tone average (PTA) frequencies of 500 Hz, 1000 Hz and 2000 Hz. If there is a masking dilemma, then the speech reception threshold module again notes that the ear could not be tested at step 1102. If, however, there is no masking dilemma, then at step 1104, the speech reception threshold module calculates the best and expected performance intensity levels. The best performance intensity level (PBTest) is the highest point on the PI curve and is the intensity level where the patient should get the most correct responses to word presentations. The 50 percent performance intensity level (PredictedSRT) is the middle point of the PI curve and is the point where the patient should correctly respond to about half of all presentations.

After PBTest and PredictedSRT have been calculated, the speech reception threshold module randomly chooses a set of word-picture pairs at step 1105. Nine word-picture pairs are used in the exemplary embodiment, but fewer or more word picture pairs may be used. Preferably, there are enough pictures to limit the possibility of correct guessing while at the same time make identifying the correct picture a simple task. In some embodiments, a method of indicating none of the above or word not understood may be provided, either in addition to or in place of one of the pictures. In the English language, the words chosen are known as "spondees" and usually have two distinctive sounding syllables uttered with equal accent on each syllable. In other languages, the words may have more than two syllables. At step 1106, the speech reception threshold module presents the set of pictures on the display screen. At step 1107, the speech reception threshold module sets the starting intensity equal to PredictedSRT. In some embodiments, the speech reception threshold module also adds a small training margin, but does not set the starting intensity to be louder than PBTest.

At step 1108, the speech reception threshold module sets the trial size equal to one for the initial intensity decrease. The speech reception threshold module thereafter initializes a count of correct responses and count of incorrect responses to zero at step 1109. Next, the speech reception threshold module checks to see if the word queue is empty at step 1110. If it is, the speech reception threshold module fills the word queue at step 1111 with non-repeating words corresponding to the pictures that are displayed. In some embodiments, the word queue contains four words randomly selected from the set of available words, but larger or smaller word queue sizes can be used. The speech reception threshold module thereafter chooses and removes one of the words from the queue at step 1112, and sets the speech masking level module at step 1113. The speech reception threshold module sets the speech masking level by calling the set speech masking level module (described below) and passing the appropriate information thereto. Once masking is initiated, the speech reception threshold module presents the word at the current intensity at step 1114, and waits for a predefined period of time for the patient to respond at step 1115. The waiting period in some embodiments is 3 seconds, but may be longer or shorter.

At step 1116, a determination is made as to whether the patient responded. If he did not respond, then at step 1117, the speech reception threshold module raises a no picture was chosen warning to the patient, and returns to step 1115 to await the patient's response. This warning may take the form of an on-screen message, a verbal indication presented via the insert earphones, or both. In some embodiments, the operator is paged if the patient repeatedly fails to respond in order to wake the patient if needed or otherwise to help him complete the picture selection task. If the patient did respond, then at step 1118, the speech reception threshold module determines whether the patient picked the correct picture. If the patient picked the wrong picture, the speech reception threshold module increments the wrong-count counter at step 1119. Otherwise, the speech reception threshold module increments the correct-count counter at step 1120. Thereafter a determination is made at step 1121 to determine if the wrong-count counter is greater than a minimum count. In some embodiments, the minimum count is the trial size divided by two. Note that for the starting intensity, since the trial size is initially one, any response will push either the wrong-count counter or the correct-count counter over the minimum count. If the wrong-count counter is not greater than the minimum count, then the speech reception threshold module determines at step 1122 whether the correct-count counter is greater than a minimum count. If the correct-count counter is also not greater than the minimum count, then no score is given at step 1123, and the speech reception threshold module returns to step 1110 to present the next word from the queue.

On the other hand, if the correct-count counter is greater than the minimum count, then at step 1124 the speech reception threshold module scores the response as speech correctly heard. Similarly, if the wrong-count counter is greater than the minimum count, then at step 1125, the speech reception threshold module scores the response as speech not correctly heard. At step 1126, the speech reception threshold module resets the trial size equal to the speech threshold trial size. In some embodiments, the speech threshold trial size is three, but may be adjusted higher as needed. At step 1127, the speech reception threshold module sets the descending intensity interval equal to the ascending intensity interval. In some embodiments, the initial descending intensity interval is set to 10 dB and the initial ascending interval is set to 5 dB.

Thereafter, the speech reception threshold module determines whether the current intensity is a threshold intensity at step 1128, by calling the threshold detection module (see FIG. 10). A determination is then made at step 1129 as to whether a threshold intensity was detected by the threshold detection module. If a threshold was indeed detected, then the speech reception threshold module concludes its procedure and returns the results to the main program module. If a threshold was not detected, then at step 1130, the speech reception threshold module determines whether the response was scored as speech correctly heard. If the response was scored a speech not correctly heard, then at step 1131, the speech reception threshold module increases the intensity by an amount equal to the ascending interval. Otherwise, if the response was scored as speech correctly heard, then the speech reception threshold module decreases the intensity by an amount equal to the descending interval at step 1132. Thereafter, the speech reception module returns to step 1109 to present the next word.

Note that in the foregoing embodiments the trial size is set to one at the start and subsequently increased. The beginning trial size is set at one so that, initially, every picture choice is scored as either heard or not heard. This lets the output level quickly descend from its starting level to a level approximately where the threshold will be. Once the patient misses a word, the trial size is increased in order to ensure that a legitimate response is received. For example, by requiring two out of three picture choices to ascertain whether the patient hears at the current level, the chance of the patient making a lucky guess is reduced (e.g., from $\frac{1}{9}$ to $\frac{2}{81}$).

Figure 12:
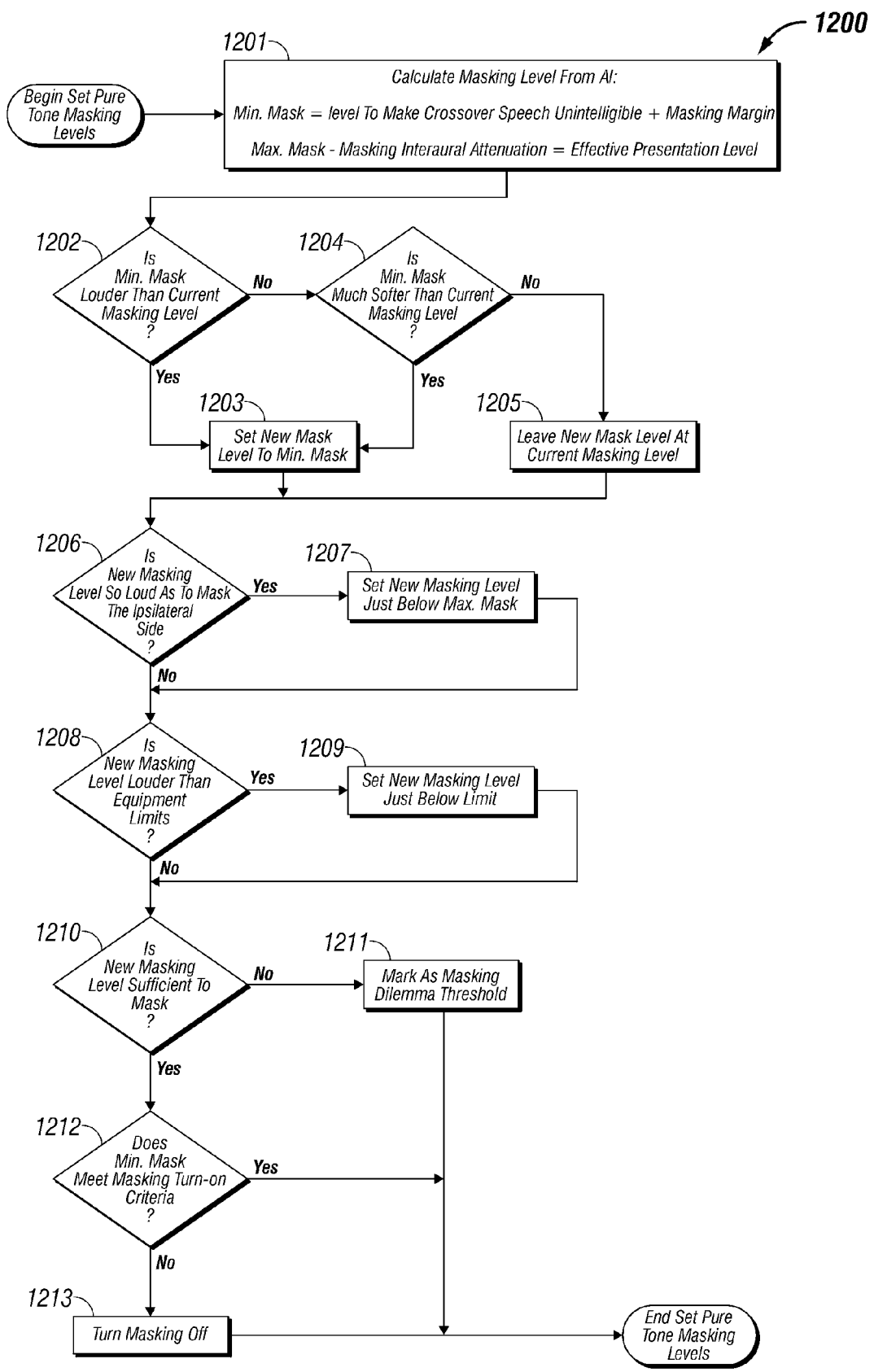
FIG. 12 illustrates an exemplary flowchart for a set speech masking levels module according to embodiments of the invention.

FIG. 12 illustrates a flowchart 1200 for an exemplary implementation of the set speech masking levels module according to some embodiments of the invention. The set speech masking levels module is called by the speech reception threshold module to determine an appropriate masking level for the non-test ear. In this regard, the set speech masking levels module has some similarities to the set pure tone masking levels module (see FIG. 9) described previously. For example, the set speech masking levels module uses a minimum masking level and a maximum masking level to control selection of the masking noise intensity. Such an arrangement helps avoid having to start selection of the masking noise intensity at a level that is too low or too high. The set speech masking levels module also implements a hysteresis in order to avoid making small, incremental changes to the masking level.

As can be seen in step 1201, the set speech masking levels module calculates a minimum masking level and a maximum masking level from the Articulation Index. In some embodiments, the minimum masking level may be defined as the level of masking noise that makes any speech crossing over to the non-test ear unintelligible. If desired, a masking margin may be added (e.g., 5 dB) to ensure that the minimum masking level will not be too low. The maximum masking level, on the other hand, may be defined as the level of masking noise beyond which, if one subtracted the masking interaural attenuation, will have the undesirable effect of masking the speech presented in the test ear.

Once these minimum and maximum masking noise intensity levels have been calculated, then at step 1202, the set speech masking levels module determines whether the minimum masking level is louder than the current masking level (e.g., from a previous iteration of the set speech masking levels module). If it is, then the set speech masking levels module sets the new masking level equal to the minimum masking level at step 1203. Otherwise, the set speech masking levels module determines at step 1204 whether the minimum masking level is much softer (e.g., more than 25 dB softer) then the current masking level. If the minimum masking level is much softer, then the new masking level is set to the minimum masking level (step 1203). On the other hand, if the minimum masking level is not much softer than the current masking level, then no change is made to the current masking level at step 1205. Note that steps 1204 and 1205 are optional steps that serve as a hysteresis to prevent small or minor changes in the masking level from being made.

At step 1206, the set speech masking levels module determines whether this new masking level is so loud as to cross over and mask the test ear. If it is, then at step 1207, the set speech masking levels module sets the new masking level just below the maximum masking level calculated above. Otherwise, at step 1208, the set speech masking levels module determines whether the new masking level will be louder than the equipment's upper intensity limit. If so, then at step 1209, the set speech masking levels module sets the new masking level to just below the upper limit of the equipment. If not, at step 1210, the set speech masking levels module determines whether the new masking level provides a sufficient level of masking noise, that is, a level equal to or greater then the previously calculated minimum masking level. If the new masking level provides an insufficient level of masking at step 1211, then the set speech masking levels module reports the new masking level as resulting in a masking dilemma, and concludes its procedure. Otherwise, the set speech masking levels module determines at step 1212 whether the new masking level meets the masking turn-on criteria (typically, 0 dB). If it does not, then masking is turned off at step 1213, and the set speech masking levels module thereafter concludes its procedure. Otherwise, the set speech masking levels module simply concludes its procedure (i.e., without turning masking off).

Figure 13:
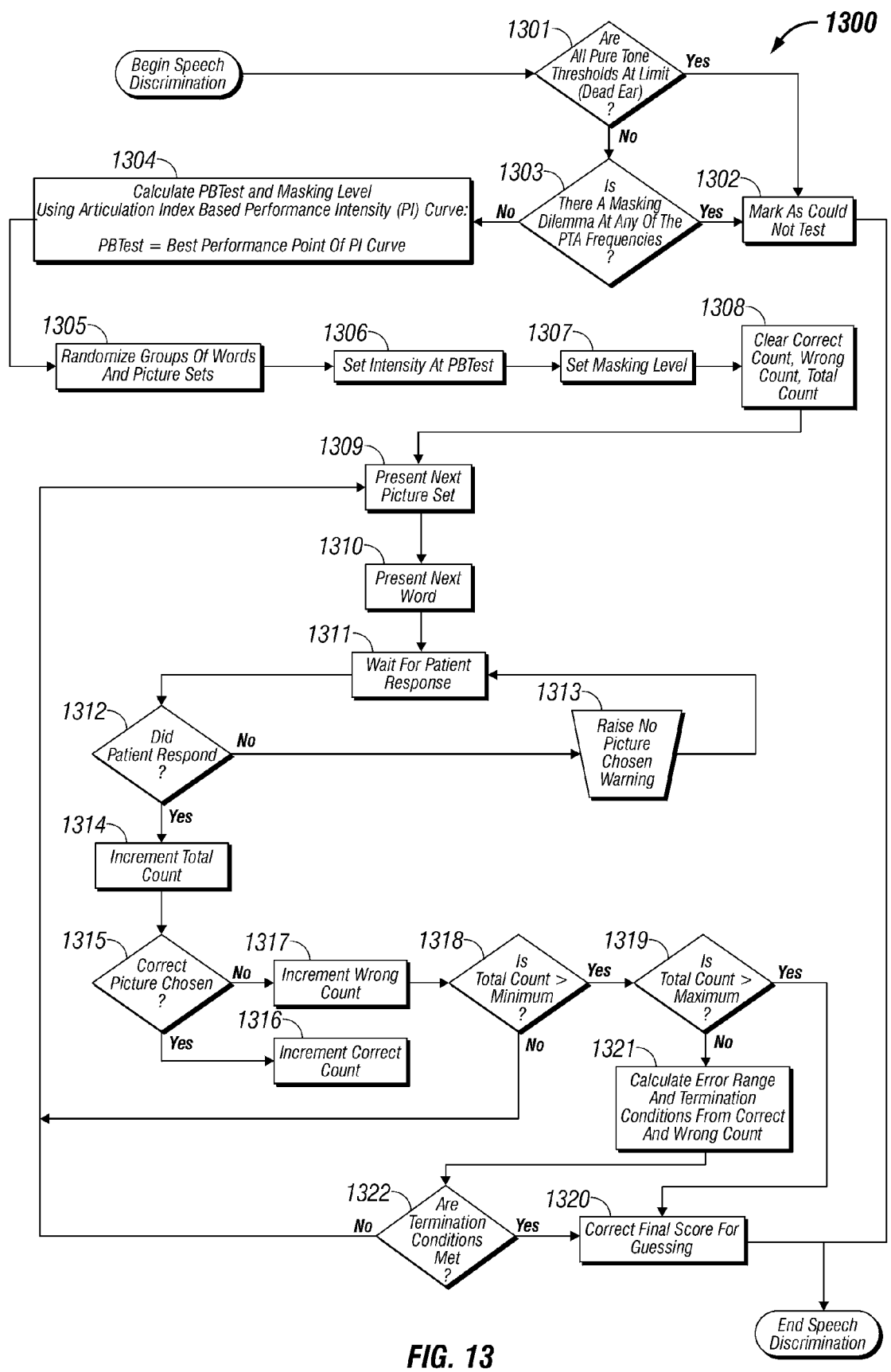
FIG. 13 illustrates an exemplary flowchart for a speech discrimination module according to embodiments of the invention.

FIG. 13 illustrates a flowchart 1300 for an exemplary implementation of the speech discrimination module according to some embodiments of the invention. The speech discrimination module is called by the main program module to perform speech discrimination testing. Unlike the pure tone threshold module or the speech reception threshold module, the speech discrimination module does not test the patient's threshold intensity. Rather, the speech discrimination module uses an intensity level that is most likely to result in the patient being able to hear the speech. The speech discrimination module thereafter determines how well the patient is able to discern between similar sounding words.

The words are preferably single syllable words that sound alike. For languages where such words are not available, appropriate adjustments may be made. A group of pictures is presented for each word. In some embodiments, the same pictures are used for each word. It is possible that some pictures will overlap from word to word, but there should be no repeats of entire picture sets. The speech discrimination module randomly chooses the groups of pictures from a large pool of such picture groups, then presents the words at a constant level, one at a time, with each group of pictures. The speech discrimination module thereafter waits for the patient to respond.

The speech discrimination module concludes it procedure when either a sufficient percentage of correct responses has been received (e.g., 85 percent), or a large enough sample has been obtained to give an accurate assessment. In some embodiments, the percentage of correct responses is evaluated on a word by word basis, with a predetermined minimum of, for example, 10 correct words. Thus, if the patient responds correctly for the first 10 words, there is no need to continue testing, and the speech discrimination module may conclude its procedure by issuing a score of 100 percent speech discrimination accuracy. Similarly, if after 50 words, the patient has only chosen 20 of the correct pictures, then again there is probably no need to continue testing. In the latter case, the speech discrimination module issues a score reflecting the appropriate speech discrimination accuracy percentage (e.g., 60 percent discrimination loss). If, on the other hand, after 15 words the patient has only given 12 correct answers, then the speech discrimination module continues with testing until the termination conditions have been met.

In the first step 1301, the speech discrimination module determines whether all of the pure tone thresholds are at the upper limit of the equipment. If they are, then that means the ear being tested is not capable of hearing any tones, i.e., the ear is a dead ear. At this point, the speech discrimination module simply notes that the ear could not be tested at step 1302. The speech discrimination module thereafter concludes its procedure and returns to the calling module.

If the ear is not a dead ear, then at step 1303, the speech reception threshold module determines whether there is a masking dilemma at any of the PTA frequencies. If there is a masking dilemma, then the speech discrimination module again notes that the ear could not be tested at step 1302. If there is no masking dilemma, then at step 1304, the speech discrimination module calculates PBTest for the patient. Recall that PBTest is the close to the highest point on the PI curve and is the intensity level where the patient should have the best chance to correctly respond to presentations. If there is no data from which to calculate PBTest, then the speech discrimination module sets the intensity level to a fairly loud volume, for example, 60 dB. Alternatively, the speech discrimination module may use an average of the pure tone intensities (if available) plus some predetermined margin (e.g., 40 dB). In other embodiments, it is also possible to let the patient adjust the intensity to a volume that he's comfortable with.

After PBTest has been calculated, the speech discrimination module randomizes and queues several groups of word-picture pairs at step 1305. In some embodiments, there are four word-picture pairs per group, and a total of about 100 groups, although these numbers may be adjusted higher or lower as needed. The four word-picture pairs within a group are selected such that the words sound similar to each other. At step 1306, the speech discrimination module sets the intensity level of the presentation equal to PBTest. At step 1307, the speech discrimination module sets the masking level so that each ear can be tested, for example, by calling the set speech masking levels module (FIG. 12). At step 1308, the speech discrimination module clears three separate counters: a correct-count counter, a wrong-count counter, and a total-count counter.

At step 1309, the speech discrimination module displays the four pictures in the group of word-picture pairs that is up next in the queue. The speech discrimination module thereafter presents one of the words from the group of four word-picture pairs at step 1310, and waits for the patient to respond at step 1311. At step 1312, the speech discrimination module determines whether the patient has responded. If there is no response, the speech discrimination module issues a no picture chosen warning to the patient at step 1313 and returns to step 1311 to await the patient's response. Otherwise, the speech discrimination module proceeds to step 1314 where it increments the total-count counter. A determination is made at step 1315 as to whether the patient chose the correct picture. If the patient chose the correct picture, then at step 1316, the correct-count counter is incremented. If the patient did not choose the correct picture, then at step 1317, the wrong-count counter is incremented.

Thereafter, at step 1318, the speech discrimination module determines whether the total-count is greater than a predetermined minimum, for example, 12 words. If the total-count is less than or equal to the predetermined minimum, then the speech discrimination module returns to step 1309, where it presents the next group of four pictures in the queue. If the total-count is greater than the predetermined minimum, then at step 1319, the speech discrimination module determines whether the total-count is greater than a predetermined maximum, for example, 100 words. If it is, then the speech discrimination module proceeds to step 1320, where it corrects the final score to compensate for any guessing. In some embodiments, the speech discrimination module compensates for guessing by determining the following: p the number of pictures displayed for each word (nominally 4); n the number of words presented; s the number of words actually correctly heard by the patient; g the number of words not correctly heard by the patient but guessed correctly; and c the number of correct picture choices made by the patient whether heard or not heard, e.g. the correct-count counter described above. By these definitions, c=s+g. Furthermore, the expected value of g is (n−s)/p, as it represents the score one would get by guessing each of the (n−s) unheard words from p pictures. Solving for s yields: s=(pc−n)/(p−1).

On the other hand, if the total-count is less than or equal to the predetermined maximum, then the speech discrimination module proceeds to step 1321, where it calculates an error range and termination conditions from the correct-count and wrong-count. At step 1322, the speech discrimination module determines whether the termination conditions have been met. If they have not, then the speech discrimination module returns to step 1309, where it presents the next set of four pictures in the queue. If the termination conditions have been met, then the speech discrimination module proceeds to step 1320, where it corrects the final score to reflect any guessing and concludes the procedure.

Figure 14:
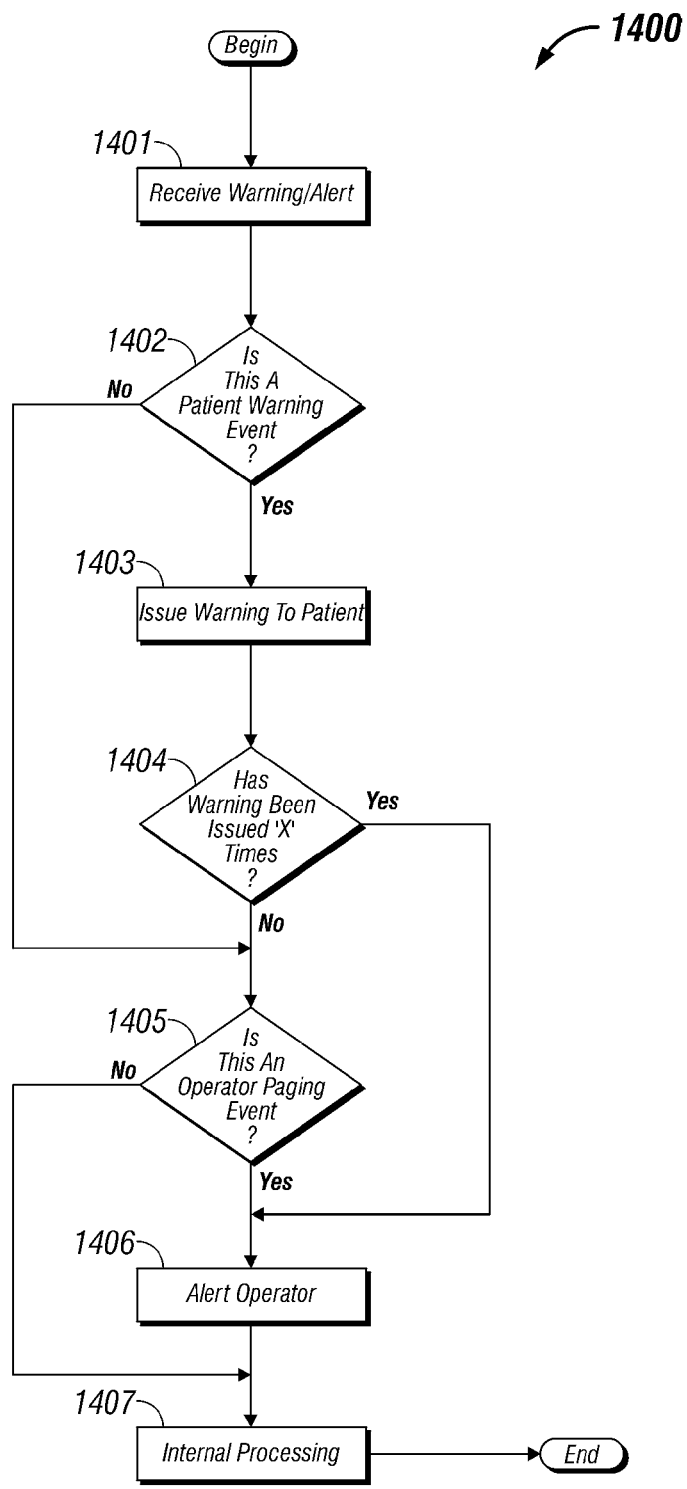
FIG. 14 illustrates an exemplary flowchart for a patient management module according to embodiments of the invention.

FIG. 14 illustrates a flowchart 1400 for an exemplary implementation of the patient management module according to some embodiments of the invention. The patient management module is called by other modules to keep the patient on track and the testing running smoothly. Thus, if the patient is not responding, or is responding too quickly, the patient management module may issue a warning to the patient. If the patient's responses indicate that there is an equipment problem, the patient management module may alert the operator. Alerting the operator may be accomplished by wireless paging or by any other suitable techniques (e.g., e-mail, console lights, buzzer, etc.).

As can be seen in FIG. 14, the first step in the flowchart 1400 is the patient management module receives an indication of a problem from a calling module at step 1401. The patient management module thereafter determines at step 1402 whether the problem is a patient warning event. If it is, then the patient management module issues warning to the patient at step 1403. In some embodiments, the patient management module references a table that specifies which types of events are patient warning events and also the particular warning message to be issued to the patient. Such patient warning events include, for example, events that trigger the warnings in steps 713, 715, 726, 923, 1117, and 1313, described above. The warning messages may also include short text messages describing the problem to the patient. The warnings may include an onscreen acknowledgment such as an "OK" button or a "Continue" button. The patient must then acknowledge the warning in order to continue.

In some embodiments, the patient management module determines whether the particular patient warning has been issued a predetermined number of times at step 1404. This may indicate that the patient is having the same difficulty over and over again. If it has, then the patient management module may page the operator at step 1406. In some embodiments, the patient management module may also page the operator if the patient has not acknowledged the warning message within a predetermined amount of time.

Otherwise, the patient management module determines whether the problem is an operator paging event at step 1405. If it is, then the patient management module pages the operator at step 1406. As before, the patient management module may reference a table that specifies which types of events are operator paging events and the messages to be issued to the operator. In some embodiments, the messages may be in the form of code words that represent different types of problems. Examples of events that are operator paging events include step 610 (e.g., the transducer is probably mounted incorrectly) and any other indication of equipment problems. Operator paging may also occur if the hearings test is not completed within a given amount of time, or if the patient requests help.

At step 1407, the patient management module performs additional processing, such as compiling the number and types of warnings that were triggered for the patient. This information may then be used to adjust the hearing test for the patient as needed, either within the current test session, or in future test sessions for this patient. For example, if the patient is routinely slow in responding during the pure tone frequency threshold test, the allotted amount of time for answering may be increased for the other tests during this session, or for future sessions.

To demonstrate the accuracy of the automated hearing test, several studies were recently conducted. In one representative study, a group of 15 patients were tested using the traditional, manually administered hearing test and also using the automated hearing test of the present invention. The results are summarized in Table 2 below. Briefly, 96 percent of all thresholds tested with the automated hearing test of the present invention were within 10 dB of the manually administered test. Likewise, 98 percent of all air thresholds, 91 percent of all bone thresholds, and 93 percent of all speech reception thresholds were within 10 dB of the manually administered test. As for speech discrimination, the average difference between the automated hearing test of the present invention and the manually administered test was 0.8 percent. Thus, in addition to being easier, more convenient, and less expensive, studies have shown that the automated hearing test of the present invention is substantially as accurate as the traditional, manually administered test.

TABLE 2

Results of Automated Hearing Test

| Pure Tone and SRT Results | Total | Air | Bone | SRT |
|---|---|---|---|---|
| Thresholds measured | 255 | 180 | 45 | 30 |
| 0 dB difference to manual (%) | 45 | 50 | 29 | 40 |
| 0-5 dB difference to manual (%) | 85 | 91 | 69 | 70 |
| 0-10 dB difference to manual (%) | 96 | 98 | 91 | 93 |
| 0-15 dB difference to manual (%) | 99 | 99 | 98 | 100 |
| Over 15 dB difference to manual (%) | 1 | 1 | 2 | 0 |

While the invention has been described with respect to a number of specific embodiments, those skilled in the art will recognize that the innovative concepts described herein can be modified and varied over a wide range of applications. Accordingly, the scope of the invention should not be limited to any of the specific exemplary teachings discussed, but is instead defined by the following claims.

What is claimed is:

1. A system for quickly and conveniently testing a patient's hearing without a sound isolation chamber and with minimal assistance from an operator, comprising:
   transducers;
   a hearing test device connected to the transducers;
   a computer connected to the hearing test device and storing an automated hearing test thereon, the automated hearing test configured to cause the computer to:
   present to the patient a list of available hearing tests, including a pure tone test, a speech reception test, and a speech discrimination test;
   prompt the patient to select one or more hearing tests from the list of available hearing tests; and
   perform each hearing test selected by the patient, wherein test data obtained during one hearing test is used in another hearing test, and test data obtained during one iteration of a hearing test is used in subsequent iterations of that hearing test;
   wherein the automated hearing test includes a pure tone frequency module configured to cause the computer to obtain a hearing threshold for a plurality of predetermined frequencies and obtain an unmasked bone conduction hearing threshold for one or more of the predetermined frequencies; and
   wherein the automated hearing test further includes a pure tone threshold module configured to cause the computer to, for each frequency being tested, obtain an unmasked bone conduction hearing threshold for the patient, determine a better ear and a poorer ear based on the unmasked bone conduction threshold, and determine one or more hearing thresholds, including at least an air conduction hearing threshold, for the better ear and the poorer ear, and issue a bone conduction threshold warning for the first frequency being tested if the air conduction hearing threshold for the better ear is larger than the unmasked bone conduction threshold by a predetermined amount.

2. The system according to claim 1, wherein the automated hearing test further causes the computer to prompt the patient to select from a list of available languages to be used for the hearing tests.

3. The system according to claim 1, wherein the computer is further connected to a tympanometer, and the list of available hearing tests includes a tympanogram test, acoustic reflex test, and otoacoustic emissions test, the automated hearing test further causes computer to acquire tympanogram or acoustic reflex data for each ear of the patient if the tympanogram or acoustic reflex test is selected.

4. The system according to claim 1, wherein the predetermined frequencies are between 250 Hz and 8000 Hz.

5. The system according to claim 4, wherein the pure tone module further causes the computer to skip the hearing threshold for certain frequencies if the hearing threshold for other frequencies meet predefined criteria.

6. The system according to claim 1, wherein the pure tone threshold module further causes the computer to determine, for each frequency being tested, a masked bone hearing threshold for the poorer ear if an air-bone gap for either ear is larger than a predetermined amount.

7. The system according to claim 6, wherein the pure tone threshold module further causes the computer to determine, for each frequency being tested, a masked bone hearing threshold for the better ear if a masked bone-unmasked bone gap for the poor ear is smaller than a predetermined amount.

8. The system according to claim 7, wherein the pure tone threshold module further causes the computer to evaluate, for each ear and frequency being tested, whether masking levels used for all hearing thresholds were correct, and to correct the masking levels as needed based on available hearing thresholds.

9. The system according to claim 1, wherein the automated hearing test further includes a pure tone intensity module configured to cause the computer to determine the one or more hearing threshold by estimating an initial intensity level to be used for each ear and frequency being tested.

10. The system according to claim 9, wherein the pure tone intensity module further causes the computer to estimate, for each ear and frequency being tested, a masking level to be used and to terminate the estimation if the estimated masking level results in a masking dilemma.

11. The system according to claim 10, wherein the pure tone intensity module further causes the computer to introduce, for each ear and frequency being tested, a random delay before presenting a tone to the patient if the estimated masking results in a masking level change.

12. The system according to claim 10, wherein the pure tone intensity module further causes the computer to introduce, for each ear and frequency being tested, a random delay before presenting a tone to the patient if the patient made any previous responses.

13. The system according to claim 10, wherein the pure tone intensity module further causes the computer to present, for each ear and frequency being tested, a tone with a frequency substantially equal to the frequency being tested.

14. The system according to claim 13, wherein the pure tone intensity module further causes the computer to, for each ear and frequency being tested, issue a false response warning to the patient if the response is received before the tone presentation and masking is being used for the first time.

15. The system according to claim 13, wherein the pure tone intensity module further causes the computer to, for each ear and frequency being tested, check whether a hearing threshold is reached upon receiving the response within an acceptable time.

16. The system according to claim 15, wherein the automated hearing test further includes a threshold detection module configured to cause the computer to check whether a hearing threshold has been reached for the intensity being used by marking the hearing threshold as an overlimit threshold if the patient fails to respond to an intensity near an equipment upper intensity limit.

17. The system according to claim 16, wherein the threshold detection module further causes the computer to calculate, for the intensity being used, a plurality of threshold indicators, including: a total number of responses at intensities within a predetermined amount of the intensity being used; a number of responses at the intensity being used; a number of non-responses at the intensity being used; a number of non-responses at a lower intensity level that were unaffected by ambient noise; a number of reversals in intensity presentation; and an average of intensity levels where reversals occurred.

18. The system according to claim 17, wherein a hearing threshold has been reached if the number of responses at the intensity being used is greater than the number of non-responses at the intensity being used, provided the number of responses at the intensity being used is greater than a predetermined minimum response and the intensity being used is greater than a previous intensity used.

19. The system according to claim 18, wherein the threshold detection module further causes the computer to increase the predetermined minimum response to allow for training.

20. The system according to claim 13, wherein the pure tone intensity module further causes the computer to measure an ambient noise and calculate an ambient noise indicator.

21. The system according to claim 20, wherein the ambient noise indicator is an ambient noise threshold shift, and the ambient noise threshold shift must be greater than the current intensity of the tone for a predetermined number of iterations before intensity of the tone is increased.

22. The system according to claim 9, wherein the automated hearing test further includes a pure tone initial intensity determination module configured to cause the computer to estimate the initial intensity level by presenting a tone to the patient at a predetermined starting intensity and increasing the intensity of the tone by a predetermined increment until the patient responds.

23. The system according to claim 1, wherein the automated hearing test is further configured to cause the computer to page the operator upon completion of the selected hearing tests.

* * * * *